(12) United States Patent
Altieri

(10) Patent No.: US 6,346,389 B1
(45) Date of Patent: Feb. 12, 2002

(54) METHOD FOR SELECTIVELY MODULATING THE INTERACTIONS BETWEEN SURVIVIN AND TUBULIN

(75) Inventor: Dario C. Altieri, Hamden, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/283,144

(22) Filed: Apr. 1, 1999

Related U.S. Application Data

(60) Provisional application No. 60/080,288, filed on Apr. 1, 1998.

(51) Int. Cl.$^7$ .............................. C12Q 1/00; C12Q 1/25; G01N 33/53; G01N 33/567; G01N 33/574

(52) U.S. Cl. .......................... 435/7.1; 435/4; 435/7.21; 435/7.23

(58) Field of Search .................. 435/4, 7.1, 7.21, 435/7.23

(56) References Cited

FOREIGN PATENT DOCUMENTS

| WO | WO95/20655 | 8/1995 | ............ C12N/15/12 |
|----|------------|--------|------------------------|
| WO | WO98/22589 | 5/1998 | ............ C12N/15/12 |

OTHER PUBLICATIONS

Li, Fengzhi et al. Control of apoptosis and mitotic spindle checkpoint by survivin. Nature 396:580–584, 1998.*

Adida et al., "Developmentally Regulated Expression of the Novel Cancer Anti–Apoptosis Gene Survivin in Human and Mouse Differentiation," *A J Pathol*, 152(1):43–49, 1998.

Ambrosini et al., "New Gene Product Prevents Apoptosis in Colon, Pancreas Cancers," *Gastroenterology*, 113(4):1060, 1997.

Ambrosini et al., "A Novel Anti–Apoptosis Gene, Survivin, Expressed in Cancer and Lymphoma," *Nature Med*, 3(8):917–921, 1997.

Ding et al., "The Spindle Pole Body of *Schizosaccharomyces pombe* Enters and Leaves the Nuclear Envelope as the Cell Cycle Proceeds," *Mol Biol Cell*, 8(8):1461–1479, 1997.

Hirio et al., "Human γ–Tubulin Functions in Fission Yeast," *J Cell Biol*, 126(6):1465–1473, 1994.

Ibrado et al., "BCl–$x_L$ Overexpression Inhibits Taxol–induced Yama Protease Activity and Apoptosis," *Cell Growth Diff*, 7(8):1087–1094, 1996.

Ireland et al., "Tubulin Alterations in Taxol–induced Apoptosis Parallel those Observed with Other Drugs," *Biochem Pharmacol*, 49(10):1491–1499, 1995.

Lajoie–Mazenc et al., "Recruitment of Antigenic gamma–Tubulin during Mitosis in Animal Cells: Presence of gamma–Tubulin in the Mitotoic Spindle," *J Cell Sci*, 107(10):2825–2837, 1994.

Martin et al., "The Role of γ–Tubulin in Mitotic Spindle Formation and Cell Cycle Progression in *Aspergillus nidulans*," *J Cell Sci*, 110(5):623–633, 1997.

Minn et al., "Expression of Bcl–$x_L$ and Loss of p53 Can Cooperate to Overcome a Cell Cycle Checkpoint Induced by Mitotic Spindle Damage," *Genes Dev*, 10(2):2621–2631, 1996.

Morgan et al., "p53 and ATM: Cell Cycle, Cell Death, and Cancer," *Adv Can Res*, 71:1–25, 1997.

Sorger et al., "Coupling Cell Division and Cell Death to Microtubule Dynamics," *Curr Opin Cell Biol*, 9(6):807–814, 1997.

Willingham et al., "Transient Mitotic Phase Localization and Bcl–2 Oncoprotein in Human Carcinoma Cells and Its Possible Role in Prevention of Apoptosis," *J Histochem Cytochem*, 42(4):441–450, 1994.

*Cell Death and Aging, Molecular Mechanisms in Molecular Biology and Biotechnology*, pp. 158–162, ed. R.A. Meyers, VCH Publishers, NY, NY 1995.

*The Encyclopedia of Molecular Biology*, p. 67, ed. J. Kendrew et al., Blackwell Science, Oxford, England, 1994.

Clem et al., "Anti–Apoptotic Genes of Baculoviruses," Cell Death and Differentiation, 3(1):9–16, 1996.

Roy et al., "The Gene for Neuronal Apoptosis Inhibitory Protein Is Partially Deleted in Individuals with Spinal Muscular Atrophy," *Cell*, 80(1):167–178, 1995.

* cited by examiner

Primary Examiner—Anthony C. Caputa
Assistant Examiner—Alana M. Harris
(74) *Attorney, Agent, or Firm*—Morgan, Lewis & Bockius LLP

(57) ABSTRACT

The present invention, based on the discovery of a new biological phenomena, provides methods and compositions for use in identifying agents which modulate the interaction between Survivin and polymerized tubulin or the mitotic spindles. Related methods and compositions can be used to modulate the interactions between Survivin and polymerized tubulin or the mitotic spindles, thereby modulating Survivin regulated apoptosis.

40 Claims, 13 Drawing Sheets

Fold Induction: 1 6.2 40

FIG. 3A

```
GAGCCACTGC ACCCGGCCTG CACGCGTTCT TTGAAAGCAG TCGAGGGGGC GCTAGGTGTG    -231

GGCAGGGACG AGCTGGCGCG GCGTCGCTGG GTGCACCGCG ACCACGGGCA GAGCCACGCG    -171

GCGGGAGGAC TACAACTCCC GGCACACCCC GCGCCGCCCC GCCTCTACTC CCAGAAGGCC    -111

GCGGGGGGTG GACCGCCTAA GAGGGCGTGC GCTCCCGACA TGCCCCGCGG CGCGCCATTA    -51

ACCGCCAGAT TTGAATCGCG GGACCCGTTG GCAGAGGTGG CGGCGGCGGC ATGGGTGCCC    10

CGACGTTGCC CCCTGCCTGG CAGCCCTTTC TCAAGGACCA CCGCATCTCT ACATTCAAGA    70

ACTGGCCCTT CTTGGAGGGC TGCGCCTGCA CCCCGGAGCG G↓GT    113
```

FIG. 3B

Consensus:
```
CDE motif:    N    N    T/G  G/C  C    G    G    N    A/G
CHR motif:    G/A  T/C  T    T    G    A    A    N    N
```

FIG. 3C

Survivin-luciferase reporter constructs

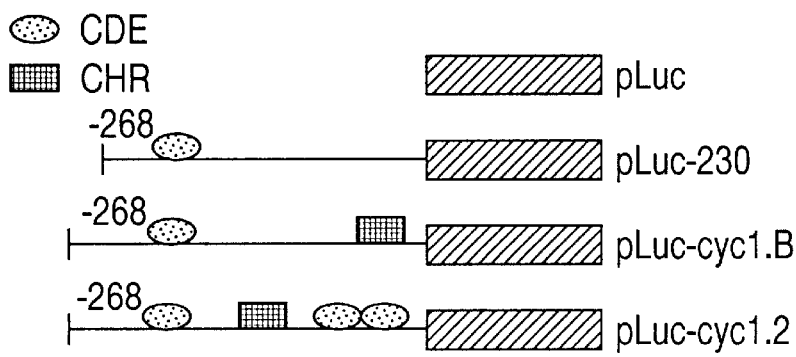

FIG. 8A (1) MGAPTLPPAWQPFLKDHRISTFKNWPFLEGCACTPERMAEAGFIHCPTENEPDLAQCFFCFKE
LEGWEPDDDPIEEHKKHSSGCAFLSVKKQFEELTLGEFLKLDRERAKNKIAKETNNKKEFEETA
KKVRRAIEQLAAMD

FIG. 8B (1) ATGGGTGCCCGACGTTGCCCTGCCTGGCAGCCCTTTCTCAAGGACCACCGCATCT
ACATTCAAGAACTGGCCCTTCTTGAGGGCTGCGCCTGCACCCCGAGCGGATGGCCGAG
GCTGGCTTCATCCACTGCCCCACTGAGAACGAGCCAGACTTGGCCCAGTGTTTCTTCTGC
TTCAAGGAGTTGGAAGGCTGGGAGCCAGATGACGACCCCATAGAGGAACATAAAAAGCAT
TCGTCCGGTTGCGCCTTTCTTCTGTCAAGAAGCAGTTTGAAGATTAACCCTTGGTGAA
TTTTTGAAACTGGACAGAGAAAGAGCCAAGAACAAAATTGCAAAGGAAACCAACAATAAG
AAGAAAGAATTTGAGGAAACTGCGAAGAAAGTGCGCCGTGCCATGCCATGAGCAGCTGGCTGCC
ATGGAT (426)

US 6,346,389 B1

METHOD FOR SELECTIVELY MODULATING THE INTERACTIONS BETWEEN SURVIVIN AND TUBULIN

RELATED APPLICATIONS

This application claims the benefit of U.S. Provisional Application Ser. No. 60/080,288, filed Apr. 1, 1998.

ACKNOWLEDGMENT OF FEDERAL SUPPORT

The research and discoveries described herein were supported by grants HL 43773 and HL 54131 from the National Institutes of Health.

TECHNICAL FIELD

The present invention, based on the discovery of a new biological phenomena, provides methods and compositions for use in identifying agents which modulate the interaction between Survivin and polymerized tubulin or the mitotic spindles. Related methods and compositions can be used to modulate the interactions between Survivin and polymerized tubulin or the mitotic spindles, thereby modulating Survivin regulated apoptosis.

BACKGROUND OF THE INVENTION

A. The Role of Survivin in Programmed Cell Death

Programmed cell death (sometimes referred to as apoptosis) is distinguishable, both morphologically and functionally, from necrosis. Programmed cell death is a natural form of death that organisms use to dispose of cells. Cells dying by programmed cell death usually shrink, rarely lyse, and are efficiently removed from the organism (rapidly recognized and engulfed by macrophages) without the appearance of inflammation (Michael Hengartner, "Cell Death and Aging, Molecular Mechanisms of," IN MOLECULAR BIOLOGY AND BIOTECHNOLOGY 158–62 (ed. R. A. Meyers, 1995)).

Apoptosis was initially used to describe a subset of programmed cell deaths sharing a particular set of morphological features which include membrane blebbing, shrinkage of cytoplasm, chromatic condensation and formation of a "DNA ladder." During apoptosis, cells lose their cell junctions and microvilli, the cytoplasm condenses and nuclear chromatin marginates into a number of discrete masses. While the nucleus fragments, the cytoplasm contracts and mitochondria and ribosomes become densely compacted. After dilation of the endoplasmic reticulum and its fusion with the plasma membrane, the cell breaks up into several membrane bound vesicles, referred to as apoptotic bodies, which are usually phagocytosed by adjacent cells. Activation of particular genes such as tumor suppressor genes in vertebrates is thought to be necessary for apoptosis to occur. Apoptosis induced by numerous cytotoxic agents can be suppressed by expression of the gene bcl-2, which produces a cytoplasmic protein Bcl-2 (THE ENCYCLOPEDIA OF MOLECULAR BIOLOGY 67 (ed. John Kendrew et al., Blackwell Science; Oxford, England, 1994).

Survivin is a 142 amino acid protein (~16.5 kDa) that is expressed in tumor cells and embryonic tissues (C. Adida et al. (1998) *Am. J. Pathol.* 152(1): 43–9; and (1997) *Gastroenterology* 113(4): 1060). The gene is located on chromosome 17q25 and is a novel member of the IAP family of apoptosis inhibitors. The nucleic acid sequence which encodes Survivin is related to that of Effector Cell Protease Receptor-1 (EPR-1) but its orientation is assigned to the antisense EPR-1 strand.

Expression of Survivin in embryonic and fetal development may contribute to tissue homeostasis and differentiation that is independent of bcl-2 (Adida et al., 1998). Aberrations of this Survivin-associated developmental pathway may result in prominent re-expression of Survivin in neoplasia and abnormally prolonged cell viability (Adida et al., 1998).

Deregulation of programmed cell death has emerged as a primary mechanism contributing to the pathogenesis of various human diseases including cancer. While the impact of anti-apoptosis genes in neoplasia has focused, for example, on the role of bcl-2 in follicular lymphoma, a potential distribution of IAP proteins, such as Survivin, has only begun to been investigated. Survivin is rarely present in adult tissues but has been detected in adenocarcinoma of the pancreas, breast adenocarcinoma, colon cancer, head and neck squamous cell carcinoma, neuroblastoma, malignant thymoma, prostate cancer, and benign prostate hyperplasia (see U.S. Ser. No. 08/975,080). This expression pattern may suggest that overexpression of survivin or alterations in survivin gene regulation may commonly occur during tumorigenisis.

B. Cell Cycle

Living organisms are composed of cells, whose growth and division require a regular sequence of events and processes that comprise the cell cycle. Some cell cycle events are continuous (e.g., synthesis of proteins and lipids), whereas others are discontinuous (e.g., DNA synthesis). Two discontinuous processes for cell survival are the replication of DNA and the segregation of chromosomes to the daughters of cell division during mitosis. If either of these steps are performed inaccurately, the daughter cells will be different from each other and will almost certainly be flawed. Segregation of chromosomes occurs during mitosis, normally a relatively brief period in the cell cycle, which culminates in the highly visible act of cell division (e.g., cytokinesis). The remainder of cell cycle comprises interphase, during which growth occurs. Chromosome replication occurs in eukaryotic cells only during interphase; and replication and segregation are mutually exclusive processes.

Interphase is subdivided into the S phase when DNA synthesis occurs and the gaps separating S phase from mitosis. G1 is the gap after mitosis, before DNA synthesis starts; G2 is the gap after DNA synthesis is complete, before mitosis and cell division. Cellular constituents direct the cell cycle by acting as regulatory elements. In some cases, cellular proteins such as p53 act as "check points" or "gate-keepers" that promote or inhibit specific steps of the cell cycle.

The Mitotic Spindle and Tubulin

The mitotic spindle is a self-organizing structure that is constructed primarily from microtubules. Among the most important spindle microtubules are those that bind to kinetochores and form the fibers along which chromosomes move. These microtubules are comprised of α-β tubulin dimers. γ-tubulin is a phylogenetically conserved component of microtubule-organizing centers that is essential for viability and microtubule function (T. Horio et al. (1994) *J. Cell Biol.* 126(6): 1465–73). It is exclusively localized at the spindle poles (also known as spindle pole bodies, SPB) in mitotic animal cells, where it is required for microtubule nucleation (M. A. Martin et al. (1997) *J. Cell Sci.* 110(5): 623–33; I. Lajoie-Mazenc et al. (1994) *J. Cell Sci.* 107(10): 2825–37). γ-tubulin is also found on osmiophilic material that lies near the inner surface of the nuclear envelope, immediately adjacent to the SPB (R. Ding et al. (1997) *Mol. Biol. Cell* 8(8): 1461–79).

One protein linked with the mitotic spindle is p53, which is a critical participant in a signal transduction pathway that mediates either a G1 arrest or apoptosis in response to DNA damage (S. E. Morgan et al. (1997) *Adv. Cancer Res.* 71:1–25). Loss of p53, in addition to suppression of apoptosis by bcl-2-related genes, may act cooperatively to contribute to genetic instability (A. J. Minn et al. (1996) *Genes Dev.* 10(2): 2621–31). The oncoprotein, Bcl-2, also has been demonstrated to be cell cycle specific, appearing in early prophase or late G2 and persisting throughout mitosis. The pattern of Bcl-2 localization shows a diffuse nuclear distribution before chromosome condensation, followed by a specific concentration of bcl-2 at the margins of condensed chromosomes in prophase, metaphase and anaphase (M. C. Willingham et al. (1994) *J. Histochem. Cytochem.* 42(4): 441–50).

Chemotherapeutics, such as taxol and the vinca alkaloids, perturb kinetochore-microtubule attachment and disrupt chromosome segregation. This activates a check point pathway that delays cell cycle progression and induces programmed cell death (P. K. Sorger et al. (1997) *Curr. Opin. Cell. Biol.* 9(6): 807–14; C. M. Ireland et al. (1995) *Biochem. Pharmacol.* 49(10): 1491–99). Taxol has been demonstrated to induce tubulin polymerization and mitotic arrest which is followed by apoptosis. Over expression of Bcl-x(L) in taxol induced cells has been demonstrated to interfere with the activation of a key protease involved in apoptosis (A. M. Ibrado et al. (1996) *Cell Growth Differ.* 7(8): 1087–94).

Although proteins that regulate apoptosis have been implicated in restraining cell cycle and controlling ploidy (chromosomal number), the effector molecules at the interface between cell proliferation and cell survival have remained elusive.

SUMMARY OF THE INVENTION

The present inventor has discovered that transcription of the survivin gene is cell cycle regulated and occurs exclusively in G2/M phase. This results in survivin re-distribution to the mitotic spindle where it mediates a default pathway of apoptosis inhibition in metaphase cells.

The present invention provides a method of identifying an agent which modulates one or more interactions between Survivin and tubulin comprising the steps of contacting Survivin and tubulin in the presence of the agent and determining whether the agent modulates one or more interactions between Survivin and tubulin, thereby identifying an agent which modulates one or more interactions between Survivin and tubulin.

The present invention further provides methods of identifying an agent which modulates one or more interactions of Survivin with the mitotic spindles of a cell, comprising the steps of contacting a mitotically active cell with the agent and determining whether the agent modulates one or more interactions of Survivin with the mitotic spindles of the cell, thereby identifying an agent which modulates one or more interactions of Survivin with the mitotic spindles.

The invention also provides methods of modulating the interaction between Survivin and tubulin comprising the step of administering an effective amount of an agent which modulates at least one interaction between Survivin and tubulin.

The invention further includes methods of modulating the interaction between Survivin and the mitotic spindles comprising administering an effective amount of an agent which modulates at least one interaction between Survivin and the mitotic spindles. The invention also provides methods of modulating apoptosis in a cell, comprising administering to the cell an effective amount of an agent which modulates the interaction between Survivin and tubulin. The invention further provides agents, compositions and peptides which modulate the interactions between Survivin and tubulin and/or the mitotic spindles.

BRIEF DESCRIPTION OF THE DRAWINGS

FIG. 1A. Survivin expression during T cell proliferation. Freshly isolated PBMC were cultivated in complete RPMI 1640 medium in the presence of phytohemagglutinin (5 µg/ml) for increasing time intervals at 37° C. At various time points, aliquots of the culture were harvested and immunoblotted with anti-Survivin mAb 8E2 (upper panel) or control mAb 2E1 recognizing the p80 subunit of the nuclear antigen Ku. PBMC proliferation determined at the various time intervals by 3HTdR incorporation was 0 (0 h), 34±8 (24 h), 927±319 (48 h), 2,577±257 (72 h), 4,061±331 (96 h), 153±45 (7 d).

FIG. 1B. Down-regulation of Survivin mRNA by serum starvation. HeLa cells ($5\times10^6$/ml) were washed, cultivated in RPMI 1640-0% FBS for increasing time intervals at 37° C. At the indicated time points, total RNA was extracted with guanidinium isothyocianate, and hybridized with a Survivin single-strand specific probe (top panel) before washing and exposure for autoradiography. Lower panel, 28S ribosomal RNA subunit for loading comparison.

FIG. 1C. Down-regulation of Survivin by cytostatic cytokines. The experimental procedures are the same as in B, except that HeLa cells were incubated with the indicated cytokine combinations for 16 h at 37° C., before RNA extraction and Northern hybridization with the Survivin single strand probe (upper panel) or control actin probe (lower panel).

FIG. 2A. Drug-induced HeLa cell synchronization. HeLa cells ($5\times10^6$/ml) were incubated with mimosine, thymidine or nocodazole for 16 h at 37° C. and analyzed for DNA content by propidium iodide staining. The markers are R1, G1; R2, S; R3, G2/M.

FIG. 2B. Cell cycle expression of Survivin mRNA. The experimental conditions are the same as in A, except that HeLa cells treated with the various synchronizing drugs were harvested, and analyzed by Northern hybridization with a Survivin specific single strand probe or control GAPDH probe. Densitometric quantitation of Survivin mRNA induction is shown at the bottom.

FIG. 2C. Cell cycle expression of Survivin protein. The experimental conditions are the same as in B, except that drug-treated HeLa cells were subjected to immunoblotting with anti-Survivin mAb 8E2 or control mAb 2E1 recognizing the p80 subunit of the nuclear antigen Ku.

FIG. 3A–FIG. 3G: Cell cycle regulation of Survivin gene expression.

FIG. 3A. DNA sequence of the proximal 5' flanking region of the Survivin gene (SEQ ID NO:1). The translational initiation codon is underlined, the beginning of the first intron is indicated by an arrow. Cell cycle regulatory CDE and CHR motifs are boxed.

FIG. 3B. Consensus DNA sequence of cell cycle regulatory CDE and CHR motifs.

FIG. 3C. Map of the Survivin deletion constructs containing one (pLuc-230), two (pLuc-cyc1.B) or four (pLuc-cyc1.2) CDE and CHR motifs.

FIG. 3D. Cell cycle transcription of the Survivin gene. HeLa cells were treated with mimosine, thymidine and nocodazole as described in FIG. 2 and transiently transfected with the various Survivin-reporter gene constructs by LipofectAMINE. 48 h after transfection, luciferase activity was determined in a luminometer and normalized for β-galactosidase activity as an internal control.

FIG. 3E. Effect of thymidine block on Survivin gene transcription. HeLa cells were synchronized by thymidine block, transfected with the Survivin-reporter gene constructs and analyzed for luciferase activity at various time intervals following release from thymidine block.

FIG. 3F. Cell cycle regulated expression of Survivin mRNA. Total RNA extracted at the indicated time intervals from HeLa cells following release from thymidine block was hybridized with a Survivin single strand probe (upper panel). Lower panel, 28S ribosomal RNA subunit for comparable loading.

FIG. 3G. Cell cycle analysis of HeLa cells released from thymidine block. The experimental procedures are the same as in E, except that HeLa cells were harvested at the indicated time intervals following release from thymidine block and analyzed for DNA content by propidium iodide staining and flow cytometry.

FIG. 4A–FIG. 4F and FIGS. 4-1(A–C): Immunolocalization of Survivin to mitotic spindles in metaphase cells.

Figure 4:
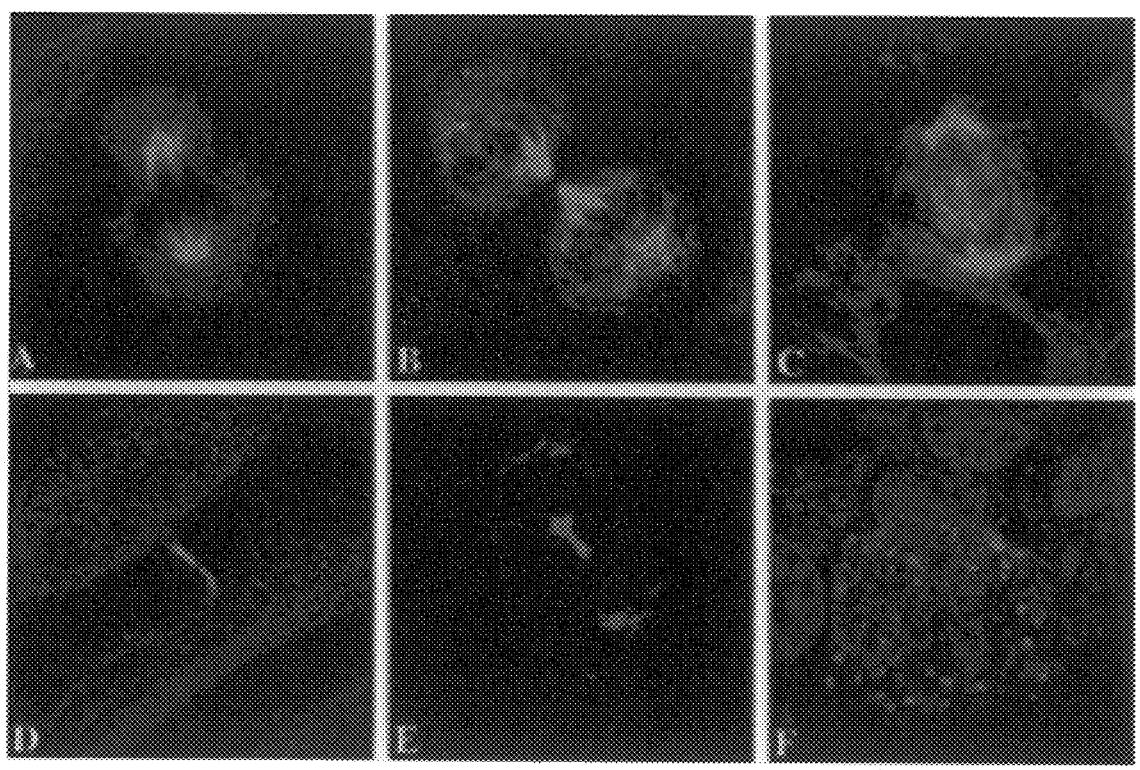
Figures 1, 4:
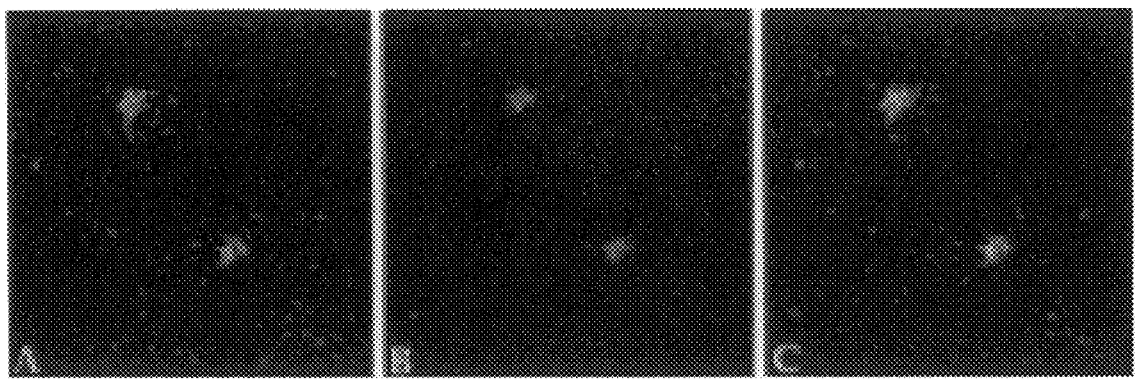

Within the paranuclear centrosomal area confocal analysis showed that Survivin had a dual location i) in brightly positive spots suggesting Survivin association with tubulin at centrioles and ii) in a cloud of material belonging to the centrosomal matrix albeit with relatively lower intensity (FIG. 4A). No obvious association with cytoplasmic microtubules was apparent but some diffuse and very weak background staining was noted in the cytoplasm. Upon taxol treatment, the association of Survivin with centrioles persisted and the diffuse cytoplasmic staining became apparent (FIG. 4B) but the pericentriolar matrix staining appeared relatively decreased. Occasionally, cytoplasmic microtubules were stained with mAb 8E2 to Survivin (not shown). For comparison the localization of γ tubulin at a centriolar pair is shown in FIG. 4C. In mitotic HeLa cells in which microtubules were stabilized and blocked by taxol treatment mAb 8E2 brightly decorated spindle fibers throughout their whole length at metaphase (FIG. 4D) suggesting association with kinetochore microtubules and also with polar microtubules at early anaphase (FIG. 4E) and midbodies at late telophase (FIG. 4F). This pattern was totally abolished by colchicine. A similar microtubular pattern was noted also in HeLa cells without any previous taxol treatment but was generally weaker and spindle fibers were blurred and much less discretely identified. However, even without taxol treatment, specific association of Survivin around spindle centrioles was noted in all dividing HeLa cells (FIG. 4-1) often forming a shell with short radiating spokes (A) around tubulin-stained centrioles (B and C).

Figure 5A:
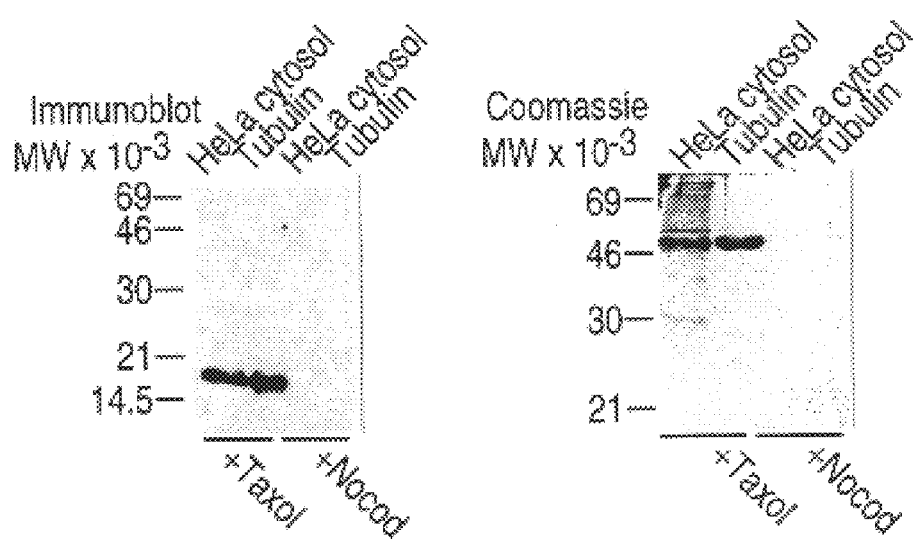
Figure 5B:
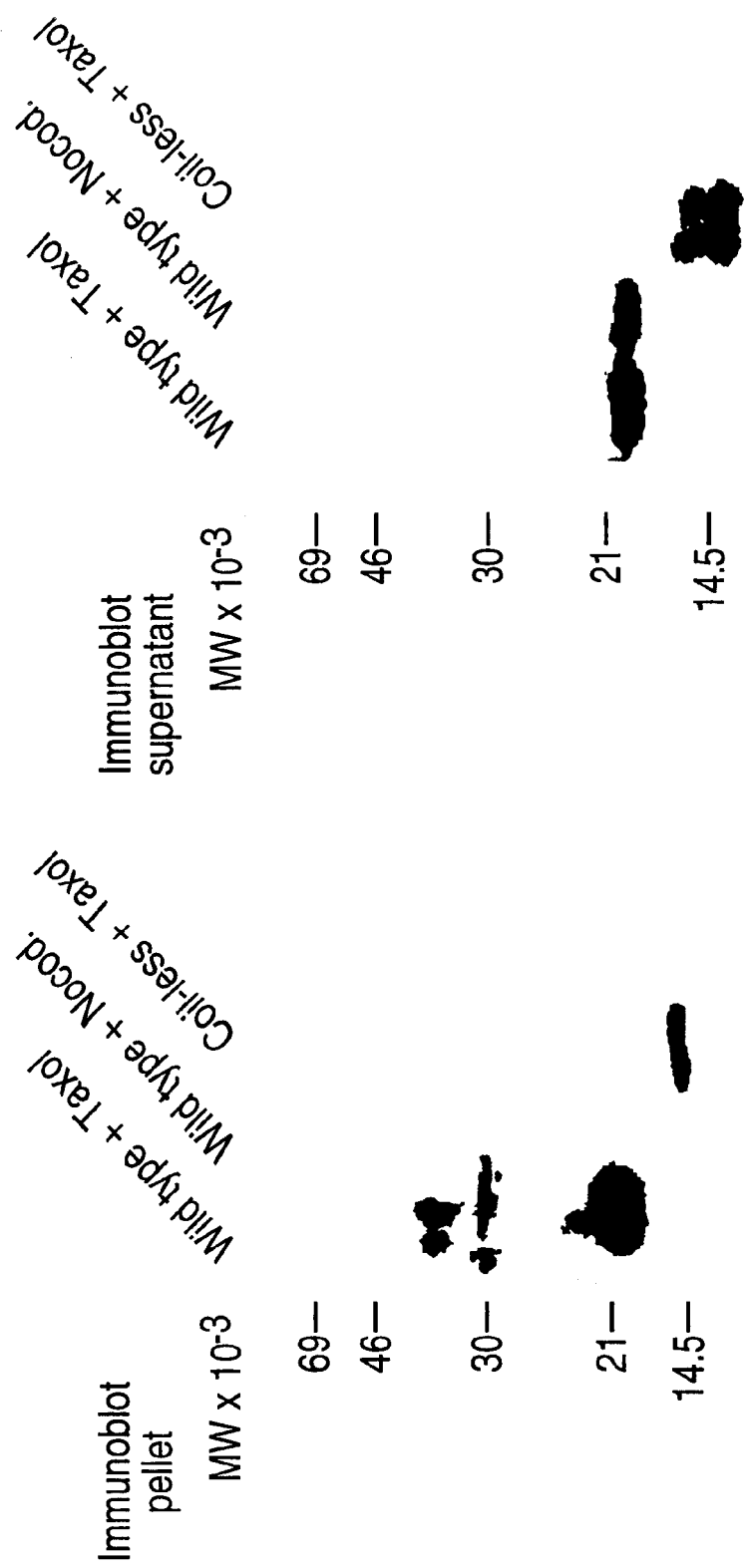

FIG. 5A–FIG. 5B: Molecular requirements of Survivin association with polymerized microtubules.

FIG. 5A. Microtubule-enriched cytosolic extracts from HeLa cells or purified brain tubulin were incubated with recombinant Survivin (4 μg) in the presence of taxol or nocodazole. Following centrifugation through a sucrose cushion, precipitated proteins in the pellet under the various conditions tested were analyzed by immunoblotting with the anti-Survivin antibody or by Coomassie blue staining.

FIG. 5B. Purified tubulin was incubated with wild type or coil-less Survivin mutant in the presence of taxol or nocodazole, centrifuged through a sucrose cushion and aliquots of the pellet or supernatant were subjected to immunoblotting with the anti-Survivin antibody. Each experiment was repeated at least three times with similar results.

Figure 6:
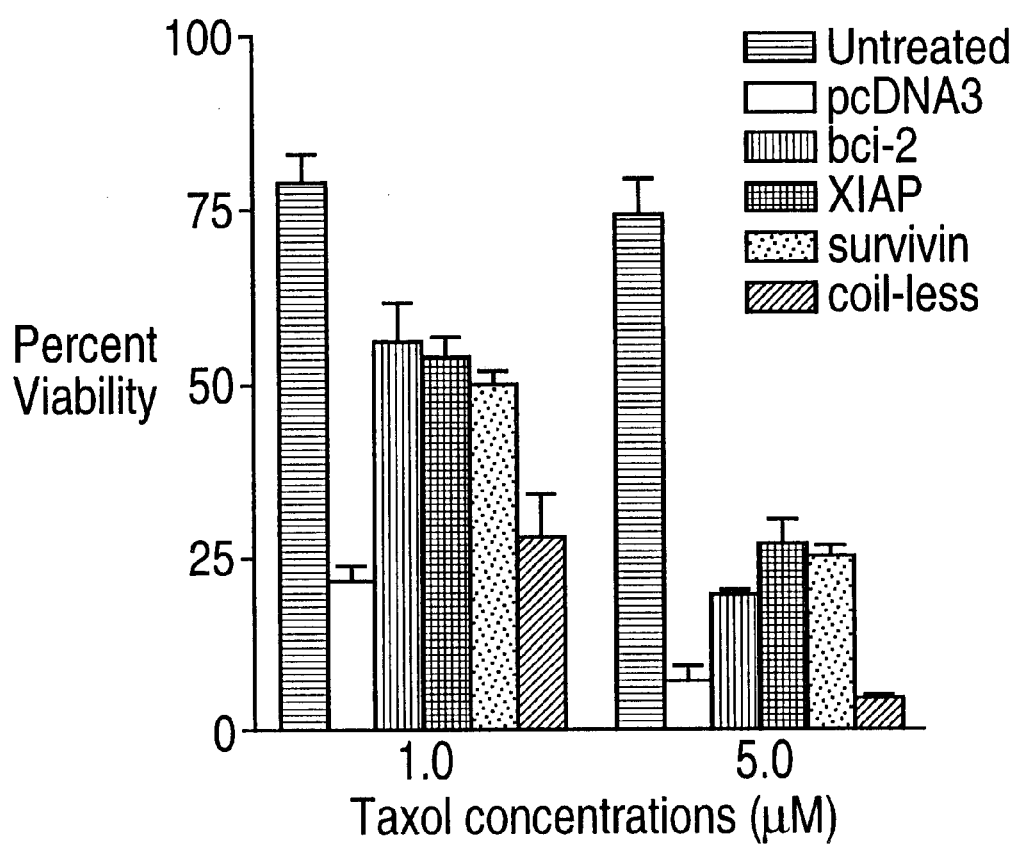

FIG. 6: Requirement of the Survivin microtubule-binding region for apoptosis inhibition. NIH3T3 cells were transiently co-transfected with the indicated cDNA constructs plus a lacZ reporter plasmid by lipofectamine. After a 24-h incubation at 37° C., cells were treated with the indicated concentrations of taxol for an additional 24-h culture at 37° C. β-galactosidase-expressing cells were scored morphologically. Data are the mean ±SEM of three independent experiments.

Figure 7A:
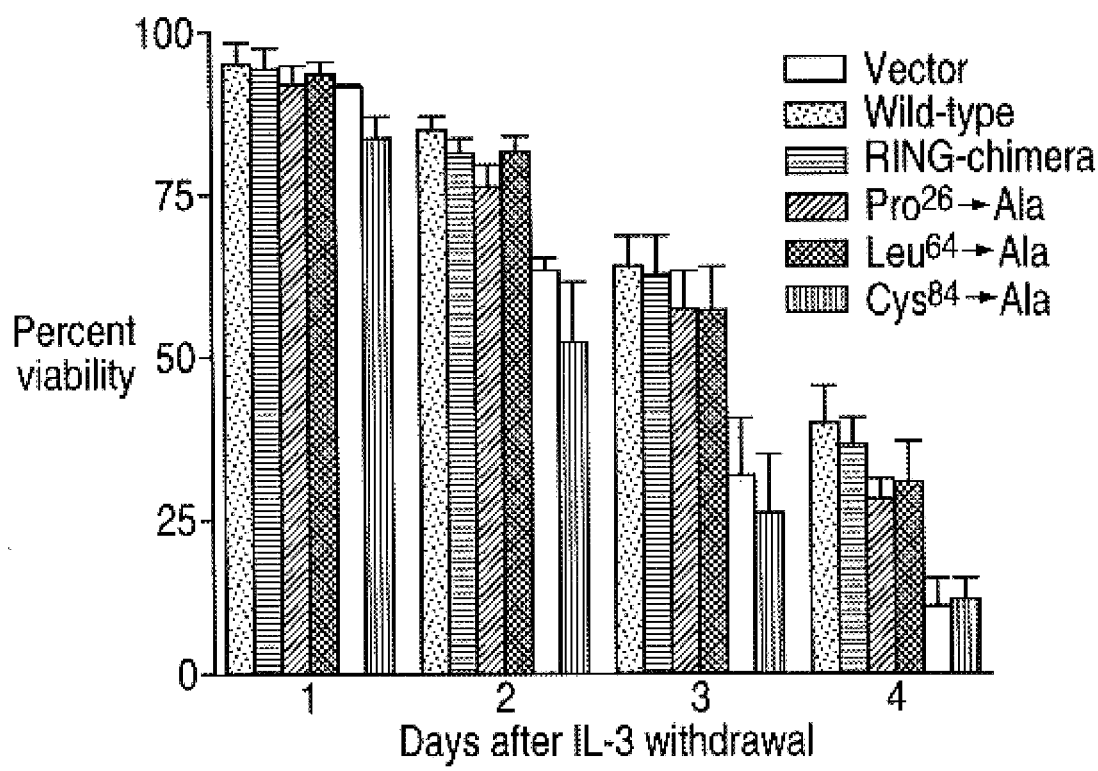
Figure 7B:
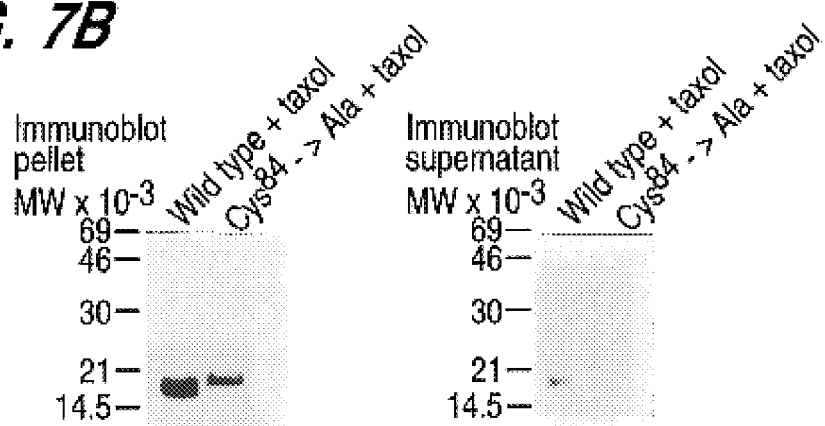

FIG. 7A–FIG. 7B: Participation of the Survivin BIR in apoptosis inhibition.

FIG. 7A. Stable BaF3 transfectants expressing wild type or the indicated Survivin BIR mutants or a Survivin/RING chimera were analyzed for apoptosis inhibition at the indicated time intervals following IL-3 withdrawal. Data are the mean ±SEM of three independent experiments.

FIG. 7B. Wild type Survivin or the loss-of-function Survivin BIR mutant Cys84→Ala were mixed with purified tubulin in the presence of taxol, followed by centrifugation through a sucrose cushion, and analysis of proteins in the pellet and supernatant by immunoblotting with the anti-Survivin antibody.

FIG. 8A–FIG. 8B. FIG. 8A is the amino acid sequence of survivin (SEQ ID NO:3). FIG. 8B is the nucleotide sequence of the open reading frame of encoding survivin (SEQ ID NO:2).

Modes of Carrying Out the Invention

I. General Description

The present invention is based in part on identifying a novel interaction between Survivin, a protein that is expressed in tumor cells and inhibits cellular apoptosis, and tubulin of the mitotic spindles of a cell.

The interactions between Survivin protein and tubulin or the mitotic spindles can be used to identify agents, or serve as a target for agents, that inhibit or stimulate Survivin mediated functions. The agents may be used to modulate Survivin mediated inhibition of cellular apoptosis, to block abnormal cell growth or to extend cell growth in culture. As used herein, modulation of apoptosis means increasing or decreasing the number of cells that would otherwise undergo apoptosis in a given cell population. This can be effected by modulating (increasing or decreasing) one or more interactions of Survivin with tubulin or the mitotic spindles present in a cell. Preferably, the given cell population in which apoptosis is to be modulated is found in a tumor or other tissue or group of cells in which beneficial effects result from the modulation. Preferably, the increase or decrease in number of cells that would otherwise undergo apoptosis in a given cell population is at least about 10%, 20%, 40% or more preferably at least about 50% of the cells in that population.

II. Specific Embodiments

A. Methods to Identify Agents that Modulate or Block Survivin/Tubulin Interactions or Survivin/Mitotic Spindle Interactions The present invention provides methods for identifying agents that, modulate, reduce or block the association of Survivin with tubulin, assembled microtubules or the mitotic spindles of a cell. As used herein, the term "tubulin" refers to all tubulin isoforms, including the α, β, and γ isoforms.

In most assay formats, Survivin is mixed with assembled microtubules in the presence and absence of an agent to be tested. After mixing under conditions that allow association of Survivin with the assembled microtubules, the two mixtures are analyzed and compared to determine if the agent modulated, increased, promoted, reduced or blocked the association of Survivin with the assembled microtubules. Agents that block or reduce the association of Survivin with the assembled microtubules will be identified by their ability to decrease the amount of association present in the sample containing the tested agent.

As used herein, an agent is said to reduce or block Survivin/assembled microtubule association when the presence of the agent decreases the extent to which or prevents the assembled microtubules from becoming associated with Survivin. One class of agents will reduce or block the association by binding to the assembled microtubules while another class of agents will reduce or block the association by binding to Survivin.

Agents that are assayed in the above method can be randomly selected or rationally selected or designed. As used herein, an agent is said to be randomly selected when the agent is chosen randomly without considering the specific sequences involved in the association of Survivin with the assembled microtubules. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action. As described above, there are two sites of action for agents that block Survivin/assembled microtubule interaction: the binding partner contact site on Survivin and the Survivin contact site on the assembled microtubules. Agents can be rationally selected or rationally designed by utilizing the peptide sequences that make up the contact sites of the Survivin/assembled microtubule. For example, a rationally selected peptide agent can be a peptide whose amino acid sequence is identical to the Survivin contact site on the assembled microtubules. Such an agent will reduce or block the association of Survivin with the assembled microtubules by binding to the assembled microtubules.

The agents of the present invention can be, as examples, peptides, small molecules, vitamin derivatives, as well as carbohydrates. A skilled artisan can readily recognize that there is no limit as to the structural nature of the agents of the present invention.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of Survivin or the assembled microtubules. Antibodies may be obtained by immunization of suitable mammalian subjects with peptides, containing as antigenic regions, those portions of the Survivin or binding partner, intended to be targeted by the antibodies. Critical regions include the contact sites involved in the association of Survivin with the assembled microtubules.

As used herein, Survivin protein (or Survivin) refers to a protein that has the amino acid sequence of human Survivin depicted in Ambrosini et al. (*Nature Med.* (1997) 3:917–921). The term "Survivin protein" also includes naturally occurring allelic variants of Survivin and naturally occurring proteins that have a slightly different amino acid sequence than that specifically recited above. Allelic variants, though possessing a slightly different amino acid sequence than those recited above, will still have the requisite ability to inhibit cellular apoptosis.

As used herein, the Survivin family of proteins refers to Survivin proteins that have been isolated from organisms in addition to humans. The methods used to identify and isolate other members of the Survivin family of proteins are readily available and described in application Ser. No. 08/975,080.

The Survivin proteins used in the assays or other embodiments of the present invention are preferably in isolated form. As used herein, a protein is said to be isolated when physical, mechanical or chemical methods are employed to remove the Survivin protein from cellular constituents that are normally associated with the Survivin protein. A skilled artisan can readily employ standard purification methods to obtain an isolated Survivin protein.

The Survivin proteins used in the present invention further include conservative variants of the Survivin proteins herein described. A conservative variant refers to alterations in the amino acid sequence that do not adversely affect the ability of the Survivin protein to bind to a Survivin binding partner, such as tubulin or assembled microtubules, and/or to inhibit cellular apoptosis. A substitution, insertion or deletion is said to adversely affect the Survivin protein when the altered sequence prevents the Survivin protein from associating with a Survivin binding partner and/or prevents the Survivin protein from inhibiting cellular apoptosis. For example, the overall charge, structure or hydrophobic/hydrophilic properties of Survivin can be altered without adversely affecting the activity of Survivin. Accordingly, the amino acid sequence of Survivin can be altered, for example to render the peptide more hydrophobic or hydrophilic, without adversely affecting the activity of Survivin.

The allelic variants, the conservative substitution variants and the members of the Survivin family of proteins retain the ability to inhibit cellular apoptosis. Such proteins will ordinarily have an amino acid sequence having at least about 75% amino acid sequence identity with the human Survivin sequence, more preferably at least about 80%, even more preferably at least about 90%, and most preferably at least about 95%. Identity or homology with respect to such sequences is defined herein as the percentage of amino acid residues in the candidate sequence that are identical with the known peptides, after aligning the sequences and introducing gaps, if necessary, to achieve the maximum percent homology, and including any conservative substitutions as being homologous. N-terminal, C-terminal or internal extensions, deletions, or insertions into the peptide sequence shall not be construed as affecting homology.

Thus, the Survivin proteins of the present invention include molecules having the amino acid sequences disclosed in Ambrosini et al.; fragments thereof having a consecutive sequence of at least about 3, 5, 10 or 15 or more amino acid residues of the Survivin protein; amino acid sequence variants of such sequence wherein an amino acid residue has been inserted N- or C-terminal to, or within, the disclosed Survivin sequence; amino acid sequence variants of the disclosed Survivin sequence, or their fragments as defined above, that have been substituted by another residue. Contemplated variants further include those containing predetermined mutations by, e.g., homologous recombination, site-directed or PCR mutagenesis, the corresponding Survivin proteins of other animal species, including but not limited to rabbit, rat, murine, porcine, bovine, ovine, equine and non-human primate species, the alleles or other naturally occurring variants of the Survivin family of proteins; and derivatives wherein the Survivin protein has been covalently modified by substitution, chemical, enzymatic, or other appropriate means with a moiety other than a naturally occurring amino acid (for example a detectable moiety such as an enzyme or radioisotope). The recombinant Survivin protein also can be used to solve the molecular structure of Survivin by 2D-NMR, circular dichroism and X-ray crystallography, thus integrating the site-directed mutagenesis approach and the rational design of specific small molecule inhibitors.

Assays of the invention may be modified or prepared in any available format, including high-throughput assays that monitor the binding of Survivin and tubulin or polymerized tubulin. In many drug screening programs which test libraries of compounds, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an inhibition of, for instance, binding between to molecules.

In one embodiment of a high-throughput screening assay, polymerized tubulin, survivin and caspase-3 may be added to the wells of a microtiter plate in the presence and absence of the agents to be tested. If a caspase-3 substrate is included in the wells, such as DEVD-containing synthetic peptides, the release of amino-4-trifluoromethylcoumerin can be assayed using continuous-reading instruments as described in Quan et al. (1995) *J. Biol. Chem.* 270:10377–10379 or Stennicke et al. (1997) *J. Biol. Chem.* 272:25719–25723. In this assay format, agents which disrupt survivin-tubulin binding will be identified by a decrease in cleavage of the DEVD-containing caspase-3 substrate peptide and a decrease in detectable amino-4-trifluoromethylcoumerin in the micotiter well.

In another embodiment of a high-throughput screening assay, the assay can be formulated to detect the ability of a test compound to inhibit binding, competitive or non-competitive, of Survivin to tubulin, polymerized tubulin or microtubules. The inhibition of complex formation may be detected by a variety of techniques. For instance, modulation of the formation of complexes can be quantitated using, for example, detectably labeled survivin such as radiolabelled (e.g. $^{32}P$, $^{35}S$, $^{14}C$ or $^{3}H$), fluorescently labeled (e.g. FITC), or enzymatically labeled survivin, by immunoassay, or by chromatographic detection.

To illustrate, there are a variety of binding assays known in the art for detecting H2-receptor antagonists based on their ability to inhibit binding of known H2 receptor ligands (including other antagonists). In one embodiment, the in vitro assay described by Norris et al. ((1985) *Agents Actions* 16:170) can be used to score for substituted N-heteroaromatics which bind to the H2-receptor (and which may be further characterized in subsequent biological assays as agonists or antagonists of that receptor). In particular, the Norris et al. assay utilizes a competitive binding assay which detects inhibition of $^{3}H$-tiotidine binding to guinea-pig cerebral cortex H2 receptors.

In certain assays, the receptor, subunits thereof, or even the other target protein to which binding is to be assessed, can be provided in a pure or semi-pure form. Typically, for those instances, it will be desirable to immobilize one of the proteins to facilitate separation of protein-protein complexes from uncomplexed forms, as well as to accommodate automation of the assay. Binding of one protein to a second protein, for instance binding of survivin to polymerized tubulin, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase(GST) fusion proteins can be adsorbed onto glutathione sepharose beads (Sigma Chemical, St. Louis, Mo.) or glutathione derivatized microtitre plates, which are then combined with the remaining labeled protein (ligand) and the test compound. The mixture is then incubated under conditions conducive to complex formation. Following incubation, the beads are washed to remove any unbound ligand, and the matrix immobilized label determined directly, or in the supernatant after the protein/ligand complexes are subsequently dissociated. When amenable, the complexes can be dissociated from the matrix, separated by SDS-PAGE, and the level of ligand found in the bead fraction quantitated from the gel using standard electrophoretic techniques.

Other techniques for immobilizing proteins on matrices are also available for use in the subject assay. For instance, either protein can be immobilized utilizing conjugation of biotin and streptavidin. Biotinylated molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the protein but which do not interfere with ligand binding can be derivatized to the wells of the plate, and the first protein, such as polymerized tubulin, trapped in the wells by antibody conjugation. As above, preparations of a ligand and a test compound are incubated in the protein-presenting wells of the plate, and the amount of protein/ligand complex trapped in the well can be quantitated. Exemplary methods for detecting such complexes, in addition to those described above, include immunodetection of complexes using antibodies reactive with the ligand, or which are reactive with the protein and compete for binding with the ligand.

Assays of the invention may also include any available in vivo based screening system to detect the interactions between two proteins. For instance, commonly available genetic systems are capable of rapidly detecting which proteins interact with a known protein, determining which domains of the proteins interact and identifying agents which modulate the interaction between two proteins. One such system is the yeast two-hybrid system wherein two proteins are expressed in yeast: one protein of interest fused to a DNA-binding domain and the other protein of interest fused to a trascriptional activation domain (Fields et al.

(1989) *Nature* 340:245; Gyuris et al. (1993) *Cell* 75:791; Harper et al. (1993) *Cell* 75:805; Serrano et al. (1993) *Nature* 366:704; and Hannon et al. (1993) *Genes & Dev.* 7:2378).

B. Apoptosis Assays

As a second step in the identification of agents which modulate at least one interaction between survivin and tubulin or survivin and the mitotic spindles of a cell, agents identified by the primary screen may then be evaluated in an apoptosis assay to determine the apoptotic activity of the agent. Specific examples of apoptosis assays are widely available in the art as exemplified in the following references. Assays for apoptosis in lymphocytes are disclosed by: Li et al. , (1995) *Science* 268:429–431; Gibellini et al. (1995) *Br. J. Haematol.* 89:24–33; Martin et al. (1994) *J. Immunol.* 152:330–42; Terai et al., (1991) *J. Clin Invest.* 87:1710–5; Dhein et al. (1995) *Nature* 373:438–441; Katsikis et al. (1995) *J. Exp. Med.* 1815:2029–2036; Westendorp et al. (1995) *Nature* 375:497; and DeRossi et al. (1994) *Virology* 198:234–44.

Assays for apoptosis in fibroblasts are disclosed by: Vossbeck et al. (1995) *Int. J. Cancer* 61:92–97; Goruppi et al. (1994) *Oncogene* 9:1537–44; Fernandez et al. (1994) *Oncogene* 9:2009–17; Harrington et al. (1994) *EMBO J.*, 13:3286–3295; and Itoh et al., (1993) *J. Biol. Chem.* 268:10932–7.

Assays for apoptosis in neuronal cells are disclosed by: Melino et al. (1994) *Mol. Cell Biol.* 14:6584–6596; Rosenblaum et al. (1994) *Ann. Neurol.* 36:864–870; Sato et al. (1994) *J. Neurobiol.* 25:1227–1234; Ferrari et al. (1995) *J. Neurosci.* 1516:2857–2866; Talley et al. (1995) *Mol. Cell Biol.* 1585:2359–2366; Talley et al. (1995) *Mol. Cell. Biol.* 15:2359–2366; and Walkinshaw et al. (1995) *J. Clin. Invest.* 95:2458–2464.

Assays for apoptosis in insect cells are disclosed by: Clem et al. (1991) *Science* 254:1388–90; Crook et al. (1993) *J. Virol.* 67:2168–74; Rabizadeh et al. (1993) *J. Neurochem.* 61:2318–21; Birnbaum et al. (1994) *J. Virol.* 68:2521–8, 1994; and Clem et al. (1994) *Mol. Cell. Biol.* 14:5212–5222.

C. Uses for Agents that Block the Association of Survivin with Assembled Microtubules/Mitotic Spindle As provided in the Background section, Survivin inhibits cellular apoptosis. Agents that reduce or block the interactions of Survivin with assembled microtubules can be used to modulate biological and pathologic processes associated with Survivin function and activity.

In detail, a biological or pathological process mediated by Survivin can be modulated by administering to a subject an agent that blocks the interaction of Survivin with assembled microtubules.

As used herein, a subject can be any mammal, so long as the mammal is in need of modulation of a pathological or biological process mediated by Survivin. The term "mammal" is meant an individual belonging to the class Mammalia. The invention is particularly useful in the treatment of human subjects.

As used herein, a biological or pathological process mediated by Survivin or Survivin binding to assembled microtubules or the mitotic spindles of a cell refers to the wide variety of cellular events mediated by Survivin. Pathological processes refer to a category of biological processes which produce a deleterious effect. For example, a pathological process mediated by Survivin is the inhibition of cellular apoptosis in tumor cells. This pathological process can be modulated using agents that reduce or block Survivin/microtubule association.

As used herein, an agent is said to modulate a pathological process when the agent reduces the degree or severity of the process. For example, an agent is said to modulate tumor cell proliferation when the agent decrease the rate or extent of cell division.

D. Administration of Agents that Modulate Survivin/Tubulin Interactions

The agents of the present invention, such as agents that block Survivin/microtubule association, can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. For example, to treat tumor cells as a means of blocking Survivin inhibition of apoptosis, an agent that blocks the interaction of Survivin with the microtubules or mitotic spindles, is administered systemically or locally to the individual being treated. As described below, there are many methods that can readily be adapted to administer such agents.

The present invention further provides compositions containing one or more agents that block Survivin/microtubule association. While individual needs vary, a determination of optimal ranges of effective amounts of each component is within the skill of the art. Typical dosages comprise 0.1 to 100 $\mu$g/kg body wt. The preferred dosages comprise 0.1 to 10 $\mu$g/kg body wt. The most preferred dosages comprise 0.1 to 1 $\mu$g/kg body wt.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice, such as chemotherapeutic agents.

E. Combination Therapy

Agents of the present invention, can be provided alone, or in combination with other agents that modulate a particular biological or pathological process. For example, an agent of the present invention that inhibits Survivin/microtubule association can be administered in combination with anti-cancer agents in methods to control cancer cell growth. As used herein, two agents are said to be administered in combination when the two agents are administered simultaneously or are administered independently in a fashion such that the agents will act at the same time.

Inhibition of Survivin activity can be used in combination with conventional chemotherapies. The timing for using a chemotherapeutic agent in combination with inhibiting Survivin activity depends upon the chemotherapeutic agent used and the tumor cell type treated. Examples of chemotherapeutic agents that can be used in combination with agents the effect Survivin activity, include, but are not limited to alkylating agents, such as cyclophosphamide (CTX; cytoxan), chlorambucil (CHL; leukeran), cisplatin (CisP; platinol) busulfan (myleran), melphalan, carmustine BCNU), streptozotocin, triethylenemelamine (TEM), mitomycin C, and the like alkylating agents; anti-metabolites, such as methotrexate MTX), etoposide (VP16; vepesid) 6-mercaptopurine (6MP), 6-thioguanine (6TG), cytarabine (Ara-C), 5-fluorouracil (5FU), dacarbazine (DTIC), and the like anti-metabolites; antibiotics, such as actinomycin D, doxorubicin (DXR; adriamycin), daunorubicin (daunomycin), bleomycin, mithramycin and the like antibiotics; alkaloids, such as vinca alkaloids such as vincristine (VCR), vinblastine, and the like; and other antitumor agents, such as taxol and taxol derivatives, the cytostatic agents glucocorticoids such as dexamethasone (DEX; decadron) and corticosteroids such as prednisone, nucleoside enzyme inhibitors such as hydroxyurea, amino acid depleting enzymes such as asparaginase, and the like diverse antitumor agents.

The use of the cytotoxic agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using the present histoculture methods. Generally, the dosage will be reduced compared to the amount used in the absence of agents the effect Survivin activity/expression.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure. All articles, publications, patents and documents referred to throughout this application are hereby incorporated by reference in their entirety.

EXAMPLES

The following procedures were employed in Examples 1–5.

Cells and cell culture. Peripheral blood mononuclear cells (PBMC) were isolated from heparinized blood collected from informed normal volunteers by differential centrifugation on Ficoll-Hypaque (Pharmacia, Piscataway, N.J.) at 400×g for 20 min at 22° C. After washes in phosphate buffered saline, pH 7.4, cells were suspended in complete RPMI 1640 medium (BioWhittaker, Walkersville, Md.) containing 10% heat inactivated fetal bovine serum (FBS, BioWhittaker). For proliferation experiments, PBMC were stimulated with phytohemagglutinin (PHA, 5 µg/ml) for increasing lengths of time at 37° C. At selected intervals, aliquots of the cell suspension were harvested, detergent solubilized and analyzed for Survivin expression by immunoblotting with an anti-Survivin antibody. In parallel experiments, aliquots of stimulated mononuclear cells were pulsed with 1 µCi/well 3HTdR (Amersham, Arlington Heights, Ill.) for 6 h at 37° C., harvested and radioactivity incorporated under the various conditions tested was determined in a scintillation β-counter. Human epithelial carcinoma HeLa cells, T lymphoma Jurkat, and contact-inhibited mouse NIH3T3 fibroblasts were obtained from American Type Culture Collection (Walkersville, Md.).

Cells were maintained in culture in complete DMEM medium (BioWhittaker) containing 10% heat inactivated FBS, non-essential amino acids, 5 mM sodium pyruvate and 5 mM L-glutamine. In some experiments, HeLa cells were washed four times in phosphate buffered saline and cultivated in 0% FBS at 37° C. Aliquots of the cell culture were harvested at 24-h intervals, and processed for RNA extraction and Northern hybridization with a Survivin-specific single strand probe. In other experiments, HeLa cells were treated with cytokines 10 ng/ml TNFα or 150 U/ml IFNγ alone or in combination for 24 h at 37° C., before determination of changes in Survivin or actin mRNA expression by Northern hybridization. For synchronization and cell cycle analysis, HeLa cells or HeLa cell transfectants were treated with mimosine (400 mM), thymidine (2 mM) and nocodazole (0.4 µg/ml), for 16 h at 37° C. according to published protocols. Alternatively, HeLa cells were synchronized to the G1/S border by a 14-h culture in the presence of 2 mM thymidine, followed by a 9-h release in complete fresh media. HeLa cells were then treated with 400 mM mimosine for 16 h at 37° C., washed and harvested at selected time intervals for RNA extraction of determination of Survivin promoter activity in transiently transfected cultures. In control experiments, HeLa cells or HeLa cell transfectants were harvested after treatment with cell cycle synchronizing drugs or after release from thymidine block and analyzed for DNA content by propidium iodide staining and flow cytometry (see below). The IL-3-dependent mouse pre-B cell line BaF3 was characterized in previous studies (Ambrosini, 1997).

Proteins and antibodies. A full-length Survivin cDNA of 1.6 kb was directionally cloned in frame in the BamHI and EcoRI sites of the prokaryotic expression vector pGEX2T (Pharmacia, Piscataway, N.J.) with transformation in BL21 E. coli strain (Pharmacia). Wild type or mutant Survivin were expressed as recombinant GST fusion proteins in the presence of 0.1 mM IPTG (Calbiochem, La Jolla, Calif.). The E. coli pellet was extracted in 25 mM Tris HCl, 50 mM glucose, 10 mM EDTA, pH 8.0, and 2 mg/ml lysozyme followed by lysis in 2% Triton X-100 and sonication. The sonicate was centrifuged at 12,000×g for 10 min at 4° C., and the supernatant applied to glutathione-Sepharose 4B column for 14 h at 4° C. with constant agitation. Wild type or mutant Survivin was released from the GST frame by overnight cleavage with thrombin (1 U/ml), neutralized with 1 mM benzamidine, and analyzed by SDS gel electrophoresis following dialysis in phosphate buffered saline, pH 7.4 and. Aliquots of wild type Survivin (100 µg) were injected in mice and hybridomas were screened against recombinant Survivin by ELISA.

Three monoclonal antibodies were isolated, established by two rounds of limiting dilution cloning and one of them (mAb 8E2) selected for further investigation. The immuno-cytochemical characterization of anti-Survivin mAb 8E2 in gastric cancer has been reported elsewhere. A rabbit antibody against the Survivin sequence A3-119 and affinity purified on a peptide-Sepharose matrix was characterized previously. Control experiments were carried out with mAb 2E1, recognizing the p80 of subunit of the nuclear antigen complex Ku. Purified tubulin was purchased from ICN Biochemicals (Aurora, Ohio).

Survivin constructs. The Survivin primers 5'CGCG-GATCCGCGTTCTTTGAAAGCAGTC3' (cyc-1, −268 to −249) (SEQ ID NO.4), 5'CCCAAGCTTTGCCGCCGC-CGCCACCTCTG3' (cyc-2, +1 to −19) (SEQ ID NO.5) and 5'CCCAAGCTTCAAATCTGGCGGTTAATGG3' (BsrBR-3, −36 to −56) (SEQ ID NO.6) carrying restriction sites were used for amplification of a Survivin genomic clone upstream of the translational initiation codon. Two PCR products designated cyc-1.2 and cyc-1.B were completely digested with BamHI and HindIII and directionally cloned upstream of the luciferase gene in the pLuc reporter vector to obtain pLuc-cyc1.2 and pLuc-cyc1.B. The pLuc-230 was constructed by inserting a 230 nt MluI/BsrBRI fragment (−268 to −39) in the SmaI site in pLuc, and confirmed for the proper orientation. A Survivin "coil-less" mutant lacking the last 41 —COOH terminus residues was generated by PCR amplification of the Survivin cDNA using oligonucleotides 5'ATCGCAAGCTTGGCGGCATGGGTGCC3' (forward) (SEQ ID NO.7) and 5'CTGAATTCAACCAAGGGTTAAT-TCTTC3' (reverse) (SEQ ID NO.8) containing the underlined restriction sites HindIII and EcoRI, respectively. The resulting product encoding Survivin Met1-Gly99 was confirmed by DNA sequencing, and directionally cloned in pcDNA3 (Invitrogen, San Diego, Calif.) or pGEX (Pharmacia) vectors for mammalian or prokaryotic expression.

Oligonucleotide-directed mutagenesis of the Survivin BIR was carried out using the Altered Site II in vitro mutagenesis system (Promega), according to the manufacturer's recommendations. The single-strand Survivin cDNA in palter vector was annealed with the following mutated oligonucleotides: 5'AAGAACTGGGCCTTCTTGGAG3' (Pro26→Ala) (SEQ ID NO.9), 5'TGCTTCAAGGAGGCG-GAAGGCTGGGA3' (Leu64→Ala) (SEQ ID NO.10), and 5'CATTCGTCCGGTGCCGCTTTCCTTTC3' (Cys84→Ala) (SEQ ID NO.11). The resulting constructs in pcDNA3 were confirmed by DNA sequencing, transfected in IL-3-dependent BaF3 cells by electroporation and stable cell lines were selected in 0.4 mg/ml G418 (GIBCO, Grand Island, N.Y.), as described previously (Ambrosini, 1997). Comparable level of expression of the various Survivin mutants in stable BaF3 transfectants was confirmed by flow cytometry with the anti-Survivin mAb 8E2. The XIAP cDNA was obtained by reverse-transcription and PCR amplification of Jurkat T cell total RNA using oligonucleotides 5'ACGGATCCAGAGAAGATGACTTTTTAAC3' (forward) (SEQ ID NO.12) and 5'ACGAATTCAACATGC-CTACTATAGAG3' (reverse) (SEQ ID NO.13). The resulting product of 1,534 nt was confirmed by DNA sequencing and inserted in pcDNA3 for transient transfection experiments. To generate a Survivin-RING chimera, the XIAP cDNA was amplified with oligonucleotides containing the underlined restriction sites. The derived product containing the XIAP carboxyl-terminal RING was fused in frame at the 3' end of the Survivin cDNA, confirmed by DNA sequencing and transfected in pcDNA3 in BaF3 cells with selection of stable transfectants.

Northern hybridization and immunoblotting. Total RNA was extracted from HeLa cells following incubation with cytostatic cytokines TNFα and IFNγ, treatment with cell cycle synchronizing drugs thymidine, mimosine and nocodazole, or at various time intervals following release from double thymidine block (2 mM) by the guanidinium isothiocyanate method. RNA samples were separated by electrophoresis on agarose-formaldehyde denaturing gels, transferred to nylon membranes (GeneScreen, DuPont de Nemours, Wilmington, Del.) and the membrane was hybridized with $^{32}$P-random-primed labeled Survivin specific single-strand probe. This probe was generated by asymmetric PCR amplification of the Survivin cDNA with 0.2 µg of oligonucleotide 5'ATGACCTCCAGAGGTTTC3'N (SEQ ID NO.14), 15 pmol dNTP (New England Biolabs), 7.5 pmol dCTP, 25 µCi $^{32}$P-dCTP (Amersham, Arlington Heights, Ill.), and 2.5 U of Taq DNA polymerase (GIBCO). Hybridization was carried out in 5×SSPE, 10×Denhardt, 1% SDS, 100 µg/ml denatured salmon sperm DNA, for 14 h at 60° C., with washes in 2×SSC, 1% SDS at 60° C. twice, and 0.2×SSC at 22° C., before exposure for autoradiography. For immunoblotting, aliquots of PHA-activated PBMC or drug-treated HeLa cells were harvested, detergent-solubilized in the presence of 0.5% Triton X-100 and 0.5% NP-40 plus protease inhibitors, and separated by electrophoresis on a 5–20% SDS polyacrylamide gradient gel under non-reducing conditions. Samples were transferred to Immobilon membranes (Millipore Corp., Bedford, Mass.) at 450 mAmps for 2 h at 4° C., blocked in TBS plus 5% dried milk, and incubated with 10 µg/ml anti-Survivin mAb 8E2 or control mAb 2E1 for 2 h at 22° C. After washes, the membrane was incubated with a 1:5000 dilution of peroxidase-conjugated goat anti-rabbit IgG and binding of the primary antibody was visualized by enhanced chemiluminescence (ECL, Amersham International, Buckinghamshire, UK), according to the manufacturer's specifications.

Transient transfection and luciferase activity. HeLa cells were seeded in 12-well plates (Costar Corp, Cambridge, Mass.) at 0.8–1.5×10$^5$ cells/well in 1 ml DMEM medium containing 10% FBS plus antibiotics. Cells were transfected at 30–60% confluency with 1 µg/well of the various plasmid DNAs previously diluted in 50 ml serum-free medium and mixed with 50 ml of Opti-MEM I containing 4 ml Lipo-fectAMINE Reagent for 30–45 minutes at 22° C. The combined mixture was overlaid on washed, serum-free HeLa cells for an additional 4–6 h at 37° C. in a 5% CO$_2$ incubator, followed by addition of complete medium and determination of luciferase activity 36–48 h after transfection.

For these experiments, HeLa cell transfectants were washed twice with phosphate buffered saline, extracted in 60 ml of reporter lysis buffer (Promega) for 10–20 min, and scraped with a rubber policeman. After centrifugation at 12,000 rpm for 15–20 sec, 5-ml aliquots of the supernatant were mixed with 10-ml of luciferase assay reagent (Promega) with determination of luciferase activity in a Lumat LB 9510 luminometer. Values were normalized for β-galactosidase activity in control lacZ transfectants determined by absorbance at OD405.

Immunofluorescence and confocal microscopy. HeLa cells were cultured on glass coverslips to confluency and treated either with Taxol (Bristol-Myers-Squibb; 10 μM in ethanol, 30 min) or with an equivalent volume of ethanol. In some experiments colchicine (Sigma; 0.2 μg/ml in PBS, 60 min) was used to depolymerize microtubules. Coverslips were fixed in chilled methanol (5 min, −20° C.) followed by a 5 sec dipping in chilled acetone. Upon air drying, coverslips were immediately rehydrated either with mAb 8E2 or with rabbit anti-γ tubulin IgGs (Sigma).

Controls were provided by irrelevant mouse or rabbit IgGs. Some control coverslips were stained with mAb 20C6 to tubulin (provided by Mary Osborn and Klaus Weber, Max Planck Institute for Biophysical Chemistry, Gottingen, Germany), sometimes in combination with rabbit anti-tubulin IgGs to check the preservation of the microtubular pattern and the relative topography of tubulin. DNA was stained by Hoechst 33342 (2 μg/ml) to identify mitotic cells in ultraviolet light prior to laser scanning. For double immunostaining, the coverslips were first incubated with a mAb followed by Texas Red (TR)-conjugated goat anti-mouse IgGs, and then with the polyclonal antibodies followed by affinity purified FITC-labeled goat anti-rabbit IgGs (Molecular Probes). After washing, coverslips were mounted in Mowiol 4-88 (Hoechst, Frankfurt/Main, Germany) and observed either in a Zeiss Axiophot microscope or analyzed with a confocal laser scanning microscope (CLSM Bio-Rad 1024). Files obtained from confocal microscopy were assembled and printed with ADOBE Photoshop 3.5.

Survivin-microtubule interaction. To determine a potential association of Survivin with tubulin, microtubules were assembled in vitro by taxol treatment using HeLa cell extracts or purified bovine brain tubulin. Subconfluent cultures of HeLa cells were harvested, washed once in phosphate buffered saline and once in MES buffer (0.1 M2-[morpholino]ethane sulphonic acid, 1 mM EGTA, 1 mM MgSO4, pH 6.6). The cell pellet was combined with 2 volumes of MES buffer and disrupted with a Dounce tissue grinder. The lysate was spun for 5 min at 12,000 rpm at 4° C. and the resulting supernatant was centrifuged at 164,000×g for 1 h at 4° C. in a TLA100 rotor (Beckman Instruments). For microtubule assembly, 200 μl aliquots of HeLa cell extracts (4 mg/ml protein) or 1 mg/ml of purified tubulin in MES buffer were supplemented with 1 mM GTP and incubated with 20 μM taxol or 40 μM nocodazole for 30 min at 37° C. Microtubule samples were then mixed with 4 μg of recombinant wild type Survivin or coil-less Survivin for an additional 30 min at 22° C. and loaded on 1 ml of 10% sucrose cushion in MES buffer containing 2 μM taxol. After centrifugation at 30,000×g for 30 min at 30° C. in a TLA100 rotor, equal amounts of the supernatants and pellets were analyzed by Coomassie blue staining and immunoblotting with the anti-Survivin antibody.

Apoptosis assay. Subconfluent cultures of NIH3T3 fibroblasts in 6-well tissue culture plates were co-transfected with 1 μg of lacZ reporter plasmid and 4 μg of various cDNA constructs, including Survivin, bcl-2, XIAP and coil-less Survivin, or control empty vector pcDNA3 using LipofectAMINE, as described above. Forty-eight hours after transfection, cells were fixed in 2% paraformaldehyde for 1 h and stained for β-galactosidase expression with 0.5 mg/ml 5-bromo-4-chloro-3-indolyl β-D-galactoside (Amersham), 5 mM potassium ferrocyanide, 5 mM potassium ferricyanide and 2 mM MgCl2 in PBS. β-Galactosidase-expressing cells were scored morphologically on an inverted microscope. In another series of experiments, BaF3 cells stably transfected with wild type or mutated Survivin constructs were washed, seeded in 96-well plates at $5 \times 10^5$/ml and cell viability was determined microscopically by trypan blue exclusion at increasing time intervals following IL-3 withdrawal, as described previously (Ambrosini, 1997).

Example 1

Survivin is Specifically Expressed in Proliferating Cells

For its abundant distribution in transformed cell lines and cancer cells, in vivo (Ambrosini, 1997), a potential role of cell proliferation in Survivin expression was investigated.

Figure 1A:
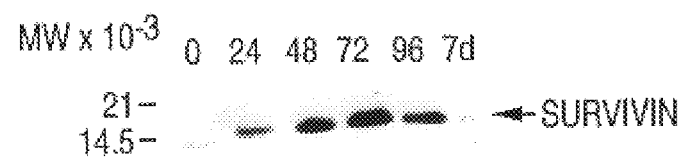
FIG. 1A–FIG. 1C: Proliferation-dependent expression of Survivin.
Figure 1A:
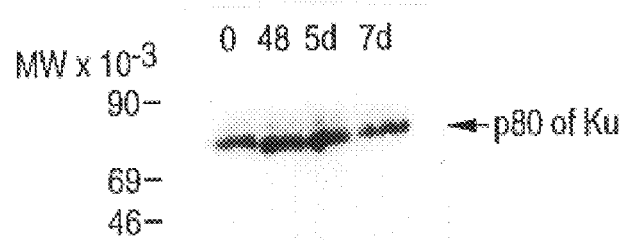

Freshly isolated PBMC were cultivated in complete RPMI 1640 medium in the presence of phytohemagglutinin (5 μg/ml) for increasing time intervals at 37° C. At various time points, aliquots of the culture were harvested and immunoblotted with anti-Survivin mAb 8E2 or control mAb 2E1 recognizing the p80 subunit of the nuclear antigen Ku. PBMC proliferation determined at the various time intervals by 3HTdR incorporation was 0 (0 h), 34±8 (24 h), 927±319 (48 h), 2,577±257 (72 h), 4,061±331 (96 h), 153±45 (7 d). In agreement with previous observations, Survivin was undetectable in resting, freshly isolated PBMC (FIG. 1A). However, mitogenic stimulation with phytohemagglutinin resulted in prominent expression of Survivin in PBMC extracts, as determined by immunoblotting with an anti-Survivin antibody (FIG. 1A). The maximum peak of Survivin expression occurred 48–72 h after stimulation, coinciding with maximal 3HTdR incorporation, and returned to undetectable levels in quiescent cultures, 7-d after stimulation (FIG. 1A, legend). No changes in expression of the p80 subunit of the nuclear antigen Ku were observed by immunoblotting under the same experimental conditions (FIG. 1A).

Figure 1B:
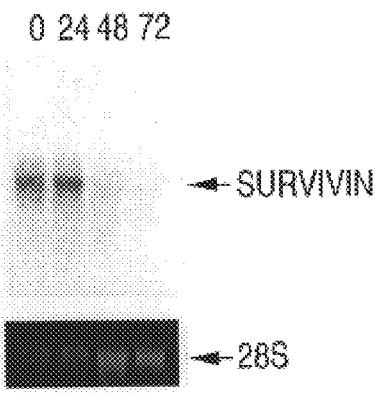

To study the effects of growth arrest induced by serum starvation, HeLa cells ($5 \times 10^6$/ml) were washed and cultivated in RPMI 1640-0% FBS for increasing time intervals at 37° C. At various time points, total RNA was extracted by the guanidinium isothyocianate method, and hybridized with a Survivin single-strand specific probe (top panel) before washing and exposure for autoradiography. 28S ribosomal RNA subunit was used as a control for loading comparison. HeLa cell growth arrest induced by serum withdrawal caused a complete disappearance of endogenous Survivin mRNA (FIG. 1B), which was de novo re-expressed following mitogen addition (not shown).

Figure 1C:
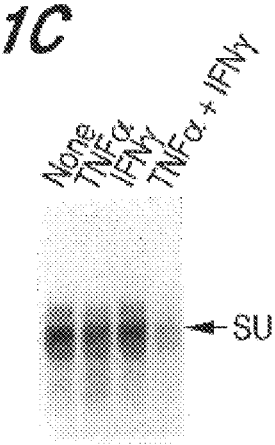
Figure 1C:
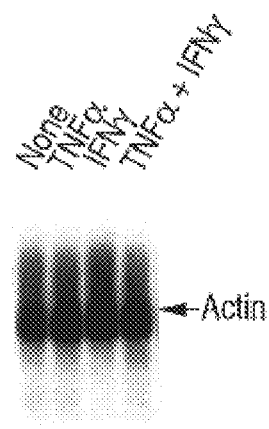

To determine the effects of cytostatic cytokines on Survivin mRNA expression, HeLa cells were washed and cultures incubated with the cytokine combinations as described above for 16 h at 37° C., before RNA extraction and Northern hybridization with the Survivin single strand probe (FIG. 1C, upper panel) or control actin probe (FIG. 1C, lower panel). Endogenous Survivin mRNA was completely down regulated following treatment of HeLa cells with the combination of cytostatic cytokines TNFα plus IFNγ (Yarden, 1986) whereas either cytokine alone was ineffective (FIG. 1C). In control experiments, no changes in expression of actin mRNA were observed under the same experimental conditions (FIG. 1C).

Example 2
Survivin Expression is Cell Cycle Dependent

Figure 2A:
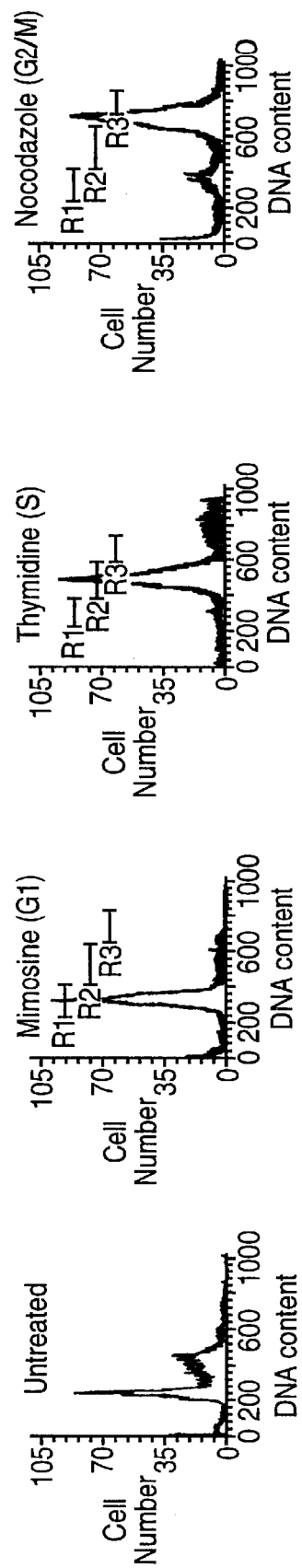
FIG. 2A–FIG. 2C: Cell cycle-dependent expression of Survivin.

The cell cycle regulation of Survivin expression was next investigated. HeLa cells were treated with various drugs known to induce arrest/synchronization at different phases of cell cycle: mimosine for late G1, thymidine for S phase and nocodozaole for the G2/M boundary. HeLa cells ($5 \times 10^6$/ml) were incubated with mimosine, thymidine or nocodazole for 16 h at 37° C. and analyzed for DNA content by propidium iodide staining as set forth in the procedures above. Analysis of DNA content under these experimental conditions revealed that mimosine arrested >90% of HeLa cells in late Gi, thymidine produced an 85% arrest in S phase and nocodazole induced a G2/M block in 75% of treated cells (FIG. 2A).

Figure 2B:
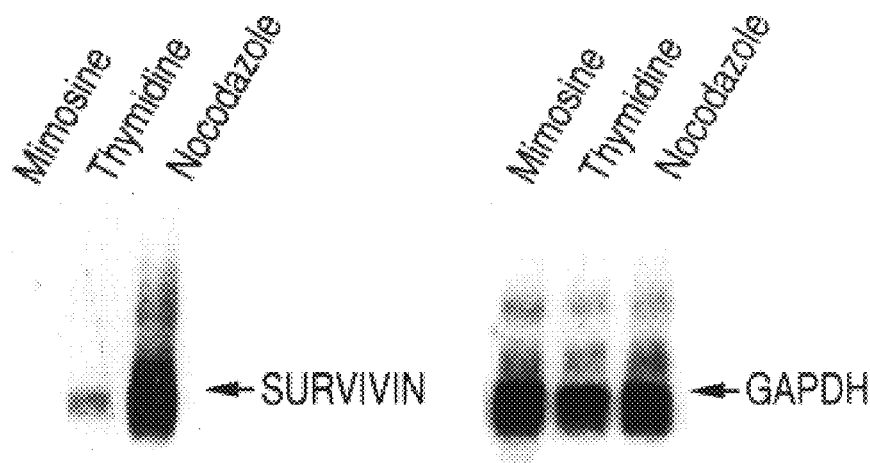

To evaluate the cell cycle expression of Survivin mRNA. The experimental conditions are the same as above except that HeLa cells treated with the various synchronizing drugs were harvested, and analyzed by Northern hybridization with a Survivin specific single strand probe or control GAPDH probe. By Northern hybridization, Survivin mRNA expression was undetectable in G1, increased by 6.2 fold over background in S phase and was dramatically up-regulated by >40 fold in G2/M phase in nocodazole-treated cells (FIG. 2B). In contrast, no differences in expression of GAPDH mRNA were observed in the various cell cycle phases (FIG. 2B). Similar results were obtained with non-transformed human umbilical vein endothelial cells (not shown).

Figure 2C:
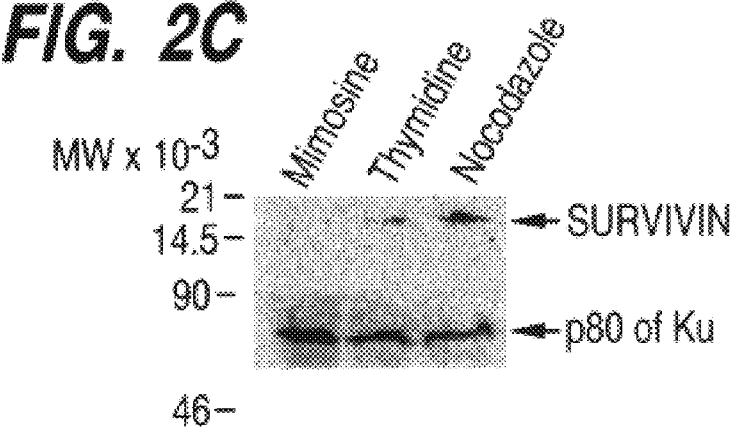

Increased expression of Survivin in G2/M-arrested HeLa cells was also demonstrated by immunoblotting with an anti-Survivin antibody (FIG. 2C), as compared with protein levels detectable in late G1 and S phase (FIG. 2C). Cells were treated as in the experimental conditions above except that drug-treated HeLa cells were subjected to immunoblotting with anti-Survivin mAb 8E2 or control mAb 2E1 recognizing the p80 subunit of the nuclear antigen Ku. In control experiments, no changes in expression of p80 of Ku were detected by immunoblotting under the same experimental conditions (FIG. 2C).

To evaluate the mechanism of cell cycle control over Survivin expression, the potential transcriptional regulation of Survivin expression in G2/M was next investigated. Inspection of the GC-rich 5' flanking region of the Survivin gene (FIG. 3A) revealed the presence of four potential cell cycle regulatory G1-repressor CDE/CHR elements. In Survivin, 3 CDE motifs and 1 CHR region matched the consensus found in other S/G2-regulated genes, including cyclins A and B, polo-like kinase, cdc2 and cdc25c (FIG. 3B).

Figure 3D:
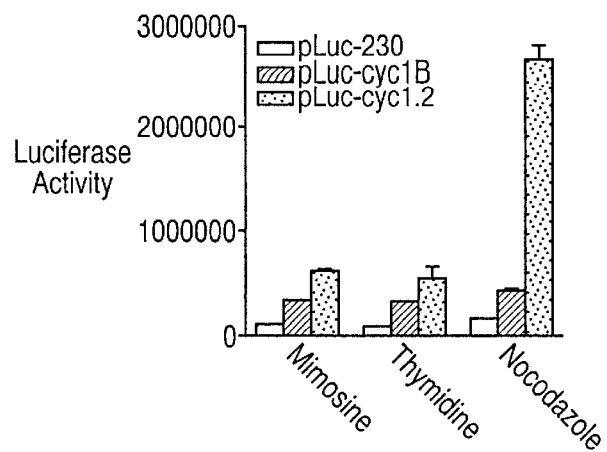

To test the potential role of these regions in cell cycle regulation of Survivin, three deletion constructs of the Survivin gene containing one, two or all four CDE/CHR motifs, respectively (FIG. 3C), were inserted upstream of a luciferase reporter gene and transfected in HeLa cells. In these experiments, deletion of all four CDE/CHR motifs (pLuc-230) or expression of the distal CDE and the proximal CHR motifs (pLuc-cyc1B) resulted in basal level of luciferase activity with no cell cycle modulation in G1-, S- or G2/M-synchronized HeLa cells (FIG. 3D). In contrast, transfection of the pLuc-cyc1.2 construct containing all four CDE/CHR motifs resulted in dramatic increase in luciferase activity in G2/M-synchronized HeLa cells, as compared with G1- or S-arrested cells (FIG. 3D).

Figure 3E:
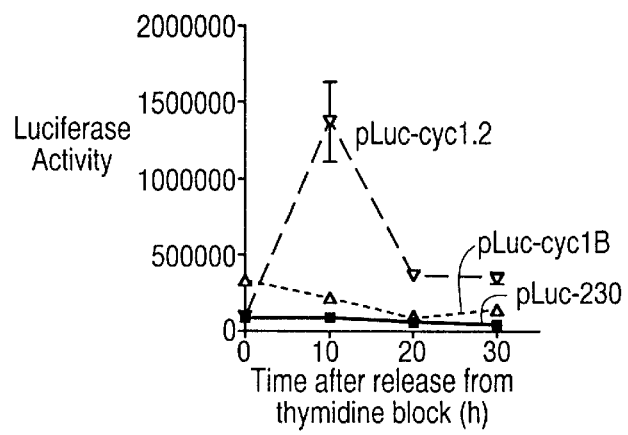
Figure 3G:
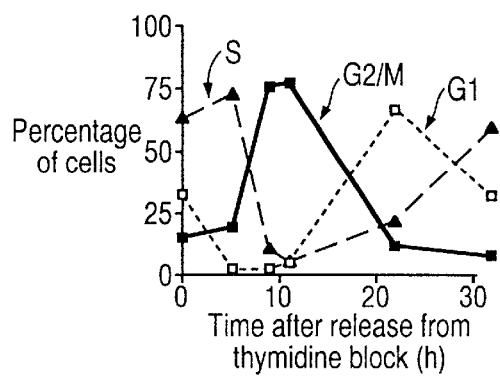
Figure 3F:
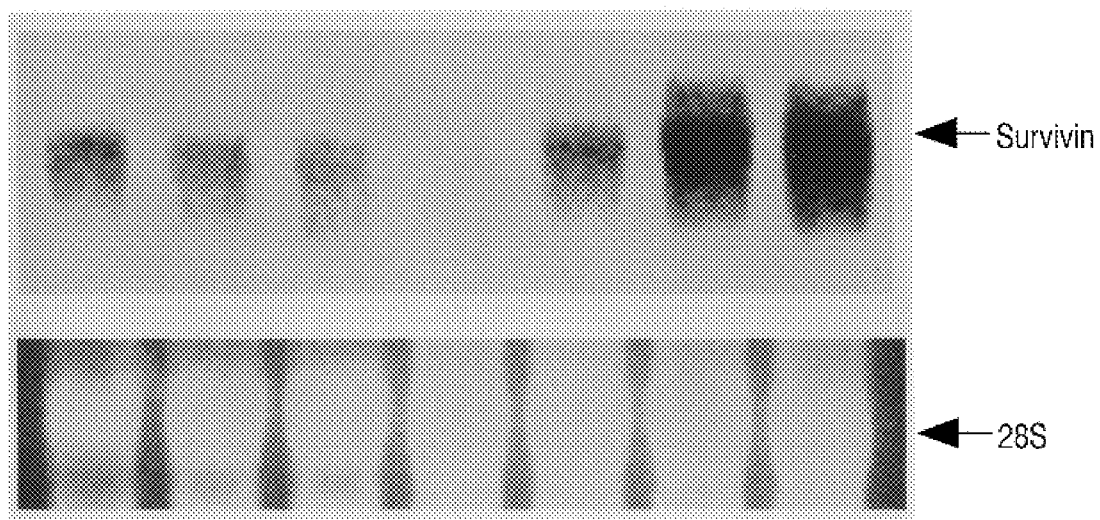

In parallel experiments, transfection of the pLuc-cyc1.2 construct in thymidine-blocked HeLa cells resulted in a maximal peak of luciferase activity 10-h after release of thymidine block (FIG. 3E), whereas control deletion plasmids pLuc-230 and pLuc-cyc1B generated cell-cycle independent basal promoter activity (FIG. 3D). Consistent with these findings, EPR-1 mRNA expression maximally increased 10–12 h after release of HeLa cells from thymidine block (FIG. 3F). In control experiments, this corresponded to the peak of G2/M phase as determined by time-course analysis of DNA content of HeLa cell following release from thymidine block (FIG. 3G).

Example 3
Survivin is Associated with the Mitotic Spindles of Metaphase Cells In control interphase HeLa cells, Survivin was predominantly concentrated at centrosomes. Within the paranuclear centrosomal area, confocal analysis showed that Survivin had a dual location i) in brightly positive spots suggesting Survivin association with tubulin at centrioles and ii) in a cloud of material belonging to the centrosomal matrix albeit with relatively lower intensity (FIG. 4A). No obvious association with cytoplasmic microtubules was apparent but some diffuse and very weak background staining was noted in the cytoplasm.

Upon taxol treatment the association of Survivin with centrioles persisted and the diffuse cytoplasmic staining became apparent (FIG. 4B) but the pericentriolar matrix staining appeared relatively decreased. Occasionally, cytoplasmic microtubules were stained with mAb 8E2 to Survivin (not shown). For comparison the localization of γ tubulin at a centriolar pair is shown in FIG. 4C. In mitotic HeLa cells in which microtubules were stabilized and blocked by taxol treatment mAb 8E2 brightly decorated spindle fibers throughout their whole length at metaphase (FIG. 4D) suggesting association with kinetochore microtubules and also with polar microtubules at early anaphase (FIG. 4E) and midbodies at late telophase (FIG. 4F). This pattern was totally abolished by colchicine. A similar microtubular pattern was noted in HeLa cells without any previous taxol treatment but was generally weaker and spindle fibers were blurred and much less discretely identified. However, even without taxol treatment, specific association of Survivin around spindle centrioles was noted in all dividing HeLa cells (FIG. 4-1) often forming a shell with short radiating spokes (A) around tubulin-stained centrioles (B and C).

Overall, data suggest that Survivin is a protein associated to MTOCs and notably to centrioles and pericentriolar matrix in G1/S HeLa cells but also binds to all spindle microtubules throughout the progression of mitotic phases indicating that Survivin affinity for microtubules and/or the amount of Survivin bound to spindle microtubules is increased in a G2/M-specific manner. The association with spindle fibers is particularly notable in taxol-stabilized microtubules suggesting that the association of Survivin with spindle microtubules is enhanced by taxol. However, even without any taxol treatment, Survivin associates to polar centrioles and exhibits a shell-like appearance with short radial spokes.

Example 4
Survivin Binds to Polymerized Tubulin/Microtubules

A potential direct association between Survivin and microtubules was next investigated. In these experiments, HeLa cell cytosolic extracts enriched in microtubules were mixed with recombinant Survivin in the presence of taxol or nocodazole, centrifuged through a sucrose cushion, and samples from supernatant or pellet under the various conditions tested were analyzed by immunoblotting with anti- Survivin antibody. Under these experimental conditions, Survivin associated with the pellet of polymerized HeLa cell microtubules or with purified brain tubulin was measured by immunoblotting FIG. 5A). This interaction was exclusively observed in the presence of microtubule-polymerizing taxol, whereas depolymerized microtubules following nocodazole treatment did not contain Survivin (FIG. 5A).

Coomassie blue staining of co-associated proteins confirmed the abundant presence of tubulin in taxol treated HeLa cell extracts or purified tubulin, but not in nocodazole-treated samples, under the same experimental conditions (FIG. 5A). The molecular requirements of Survivin association with microtubules were next investigated. As opposed to all IAP proteins except NAIP (Roy, 1995), Survivin lacked a carboxyl-terminal RING finger, and contained instead a charged region of 43 amino acids, potentially organized as a coiled-coil. The potential role of the Survivin coiled-coil in microtubule interaction was investigated. In co-sedimentation and quantitative immunoblotting experiments, the ability of a Survivin coil-less mutant to bind to taxol-polymerized tubulin or HeLa cell extracts was reduced by >80%, as compared with wild type Survivin, under the same experimental conditions (FIG. 5B).

Consistent with the data presented above, no association of wild type Survivin with non-polymerized, nocodazole-treated samples was demonstrated (FIG. 5B). By Coomassie staining, comparable amounts of polymerized tubulin were demonstrated in the pellet of taxol-treated samples in the presence of wild type or coil-less Survivin (not shown). Consistent with these observations, the majority of Survivin coil-less mutant was detected in the supernatant of taxol treated samples by immunoblotting, and similar results were observed with wild type Survivin in nocodazole-treated samples (FIG. 5B). A variable degree of depletion of wild type Survivin was observed in the supernatant of taxol-treated samples (FIGS. 5B and 7B).

Example 5
The Carboxy-terminus of Survivin is Required for Apoptosis Inhibition

The potential role of Survivin association with the mitotic spindle for apoptosis inhibition was next investigated. Treatment of NIH3T3 cells with increasing concentrations of taxol resulted in dose-dependent induction of apoptosis (FIG. 6A), in agreement with previous observations. In contrast, transfection of NIH3T3 cells with bcl-2, XIAP or wild type Survivin resulted in increased viability after taxol treatment, as compared with control transfectants with pcDNA3 vector (FIG. 6A). Under these experimental conditions, transient transfection of the Survivin coil-less mutant failed to protect NIH3T3 cells from apoptosis induced by different concentrations of taxol (FIG. 6A). A more detailed mutational analysis of Survivin inhibition of apoptosis was carried out in stable IL-3-dependent BaF3 transfectants. Stable BaF3 transfectants expressing wild type, Survivin BIR mutants or a Survivin RING chimera as set forth in the above experimental procedures were analyzed for apoptosis inhibition at the indicated time intervals following IL-3 withdrawal. Ala mutagenesis of Cys84 in the Survivin BIR was associated with complete loss of anti-apoptotic function following IL-3 withdrawal (FIG. 7A). In contrast, Survivin BIR mutants Leu64→Ala or Pro26→Ala or a Survivin/RING chimera were as effective as wild type Survivin in protecting BaF3 transfectants from apoptosis induced by IL-3 withdrawal (FIG. 7A). Comparable levels of expression of wild type and the various Survivin mutants in BaF3 transfectants were demonstrated by flow cytometry with the anti-Survivin antibody (not shown).

Co-sedimentation experiments were also performed to analyze the role of Survivin association with the mitotic spindle and apoptosis inhibition. Briefly, wild type Survivin or the loss-of-function Survivin BIR mutant Cys84→Ala were mixed with purified tubulin in the presence of taxol, followed by centrifugation through a sucrose cushion, and analysis of proteins in the pellet and supernatant by immunoblotting with the anti-Survivin antibody. In co-sedimentation experiments, the loss-of-function Survivin BIR mutant Cys84→Ala associated with taxol-treated tubulin, in a reaction quantitatively indistinguishable from that of wild type Survivin (FIG. 7B). Consistent with the data reported above, this was associated with nearly complete depletion of wild type and mutant Survivin from the supernatant of taxol-treated samples, by immunoblotting (FIG. 7B).

In summary, the integrity of two domains appear to be required for Survivin mediated inhibition of apoptosis. The above results demonstrate that the association of Survivin with the mitotic spindle is required for apoptosis inhibition because a coil-less Survivin mutant fails to bind to microtubules and does not protect 3T3 cells from apoptosis induced by taxol. However, the results also demonstrate that a Survivin point-mutant in the BIR domain Cys84 to Ala also fails to protect cells from apoptosis but still retains the ability of the protein to bind to tubulin. This indicates that the integrity of the two domains in Survivin, the BIR and the coiled-coil are required for inhibition of apoptosis. It is possible that the Survivin BIR may be required for a direct inhibition of caspases as it has been shown for other LAP molecules. This would suggest that during mitosis, the mitotic spindle may be susceptible to cleavage by caspases (caspase-3). In this model, Survivin would bind to tubulin through its coiled-coil domain and would inhibit caspase activity through its BIR domain. Mutations in either region would result in loss of anti-apoptotic function.

Example 6
Method of Identifying an Agent which Modulates One or More Interactions Between Survivin and Tubulin The interactions described above between Survivin and tubulin allow for the development of assays to identify an agent which modulates one or more interactions between Survivin and tubulin. Such assays use, as common steps, a step of contacting Survivin and tubulin in the presence of the agent and a step of determining whether the agent modulates one or more interactions between Survivin and tubulin. Any means to detect Survivin/tubulin interactions may be used.

In one format, the ability of an agent to modulate the binding of Survivin to polymerized tubulin (microtubules) may be assayed. Microtubules are assembled in vitro by taxol treatment using HeLa cell extracts or purified bovine brain tubulin. Subconfluent cultures of HeLa cells are harvested, washed once in phosphate buffered saline and once in MES buffer (0.1 M2-[morpholino]ethane sulphonic acid, 1 mM EGTA, 1 mM MgSO4, pH 6.6). The cell pellet is combined with 2 volumes of MES buffer and disrupted with a Dounce tissue grinder. The lysate is spun for 5 min at 12,000 rpm at 4° C. and the resulting supernatant centrifuged at 164,000×g for 1 h at 4° C. in a TLA100 rotor (Beckman Instruments).

For microtubule assembly, 200 µl aliquots of HeLa cell extracts (4 mg/ml protein) or 1 mg/ml of purified tubulin in MES buffer are supplemented with 1 mM GTP and incubated with 20 µM taxol or 40 µM nocodazole for 30 min at 37° C. Microtubule samples are then mixed with 4 µg of recombinant wild type Survivin or coil-less Survivin in the presence and absence of the agent to be tested for an additional 30 min at 22° C. and loaded on 1 ml of 10% sucrose cushion in MES buffer containing 2 µM taxol.

After centrifugation at 30,000×g for 30 min at 30° C. in a TLA100 rotor, equal amounts of the supernatants and pellets are analyzed by Coomassie blue staining and immunoblotting with the anti-Survivin antibody. The ability of the agent to modulate binding of Survivin to the assembled microtubules is then determined by comparing the amount or quantity of Survivin bound to the assembled microtubules in the samples exposed to the agent and the amount or quantity of Survivin bound to the assembled microtubules in the control (non-agent exposed) sample.

In another format, the ability of an agent to modulate the binding of Survivin to polymerized tubulin can be assayed by mixing HeLa cell extracts (4 mg/ml protein) or 1 mg/ml of purified tubulin in MES buffer supplemented with 1 mM GTP and incubated with 20 µM taxol or 40 µM nocodazole for 30 min at 37° C. with 4 µg of recombinant wild type Survivin in the presence and absence of the agent to be tested for an additional 30 min at 22° C. The samples are then exposed to tubulin specific antibodies attached to a solid support, the support washed, and bound Survivin detected with the Survivin specific antibody mAb 8E2. The ability of the agent to modulate binding of Survivin to the assembled microtubules is then determined by comparing the amount or quantity of Survivin bound to the assembled microtubules in the samples exposed to the agent and the amount or quantity of Survivin bound to the assembled microtubules in the control (non-agent exposed) sample.

Example 7

Method of Identifying an Agent which Modulates One or More Interactions Between Survivin and the Mitotic Spindles of a Cell.

The interactions described above between Survivin and the mitotic spindles of a cell allow for the development of assays to identifying an agent which modulates one or more interactions between Survivin and the mitotic spindles. Such assays use as common steps, a step of contacting Survivin and the mitotic spindles, preferably in a cell, in the presence of the agent, and a step of determining whether the agent modulates one or more interactions between Survivin and the mitotic spindles. Any means to detect Survivin/mitotic spindle interactions may be used.

In one format, HeLa cells are cultured on glass coverslips to confluency and treated either with taxol in the presence and absence of the agent to be tested (Bristol-Myers-Squibb; 10 µM in ethanol, 30 min) or with an equivalent volume of ethanol. In some experiments colchicine (Sigma; 0.2 µg/ml in PBS, 60 min) is used to depolymerize microtubules. Coverslips are fixed in chilled methanol (5 min, −20° C.) followed by a 5 sec dipping in chilled acetone. Upon air drying coverslips are immediately rehydrated either with mAb 8E2 or with rabbit anti-tubulin IgGs (Sigma). Controls are provided by irrelevant mouse or rabbit IgGs. Some control coverslips may also be stained with mAb 20C6 to tubulin (provided by Mary Osborn and Klaus Weber, Max Planck Institute for Biophysical Chemistry, Göttingen, Germany), sometimes in combination with rabbit anti-tubulin IgGs to check the preservation of the microtubular pattern and the relative topography of tubulin. DNA may be stained by Hoechst 33342 (2 µg/ml) to identify mitotic cells in ultraviolet light prior to laser scanning. For optional double immunostaining, the coverslips are first incubated with a mAb followed by Texas Red (TR)-conjugated goat anti-mouse IgGs, and then with the polyclonal antibodies followed by affinity purified FITC-labeled goat anti-rabbit IgGs (Molecular Probes). After washing, coverslips are mounted in Mowiol 4-88 (Hoechst, Frankfurt/Main, Germany) and observed either in a Zeiss Axiophot microscope or analyzed with a confocal laser scanning microscope (CLSM Bio-Rad 1024).

The ability of the agent to modulate binding of Survivin to the mitotic spindles is then determined by comparing the amount or quantity of Survivin bound to the mitotic spindles of a cell in the samples exposed to the agent and the amount or quantity of Survivin bound to the mitotic spindles in the control (non-agent exposed) sample.

Although the present invention has been described in detail with reference to examples above, it is understood that various modifications can be made without departing from the spirit of the invention. Accordingly, the invention is limited only by the following claims.

Additional References

The following articles are hereby incorporated by reference in their entirety:

1. Nagata, S. (1997) Apoptosis by death factor. *Cell* 88:355–365
2. Vaux, D. L., Haecker, G. and Strasser, A. (1994) An evolutionary perspective on apoptosis. *Cell* 76:777–779
3. Thompson, C. B. (1995) Apoptosis in the pathogenesis and treatment of disease. *Science* 267:1456–1462
4. Yang, E. and Korsmeyer, S. J. (1996) Molecular thanatopsis: a discourse on the BCL2 family and cell death. *Blood* 88:386–401
5. Duckett, C. S., Nava, V. E., Gedrich, R. W., Clem, R. J., Van Dongen, J. L., Gilfillan, M. C., Shiels, H., Hardwich, J. M. and Thompson, C. B. (1996) A conserved family of cellular genes related to the baculovirus iap gene and encoding apoptosis inhibitors. *EMBO J.* 14:2685–2694
6. Reed, J. C. (1997) Double identity for proteins of the Bcl-2 family. *Nature* 387:773–776
7. Liston, P., Roy, N., Tamal, K., Lefebvre, C., Baird, S., Cherton-Horvat, G., Farahani, R., McLean, M., Ikeda, J.-E., MacKenzie, A. and Komeluk, R. G. (1996) Suppression of apoptosis in mammalian cells by NAIP and a related family of LAP genes. *Nature* 379:349–353
8. Uren, A. G., Pakusch, M., Hawkins, C. J., Puls, K. L. and Vaux, D. L. (1996) Cloning and expression of apoptosis inhibitory protein homologs that function to inhibit apoptosis and/or bind tumor necrosis factor receptor-associated factors. *Proc. Natl. Acad. Sci. USA* 93:4974–4978
9. Deveraux, Q. L., Takahashi, R., Salvesen, G. S. and Reed, J. (1997) X-linked IAP is a direct inhibitor of cell-death proteases. *Nature* 388:300–304
10. Roy, N., Mahadevan, M. S., McLean, M., Shutler, G., Yaraghi, Z., Farahani, R., Baird, S., Besner-Johnston, A., Lefebvre, C., Kang, X., Salith, M., Aubry, H., Tamai, K., Guan, X., Ioannou, P., Crawford, T. O., de Jong, P. J., Surh, L., Ikeda, J.-E., Komeluk, R. G. and MacKenzie, A. (1995) The gene for neuronal apoptosis inhibitory protein is partially deleted in individuals with spinal muscular atrophy. *Cell* 80:167–178
11. Rao, L., Debbas, M., Sabbatini, P., Hockenberry, D., Korsmeyer, S. and White, E. (1993) The adenovirus E1A proteins induce apoptosis, which is inhibited by the E1B 19-kDa and bcl-2 proteins. *Proc. Natl. Acad. Sci. U.S.A.* 89:7742–7746
12. Evan, G. I., Brown, L., Whyte, M. and Harrington, E. (1995) Apoptosis and the cell cycle. *Curr. Opin. Cell Biol.* 7:825–834
13. Weinberg, R. A. (1995) The retinoblastoma protein and cell cycle control. *Cell* 81:323–330

14. Wu, X. and Levine, A. J. (1994) p53 and E2F-1 cooperate to mediate apoptosis. *Proc. Natl. Acad. Sci. U.S.A.* 91:3602–3606
15. Field, S. J., Tasi, F.-Y., Kuo, F., Zubiaga, A. M., Kaelin, W. G., Jr., Livingston, W. G., Jr., Orkin, S. H. and Greenberg, M. E. (1996) E2F1 functions in mice to promote apoptosis and suppress proliferation. *Cell* 85:549–561
16. Evan, G. I., Wyllie, A. H., Gilbert, C. S., Littlewood, T. D., Land, H., Brooks, M., Waters, C. M., Penn, L. Z. and Hancock, D. C. (1992) Induction of apoptosis in fibroblasts by c-myc protein. *Cell* 69:119–128
17. Galaktionov, K., Chen, X. and Beach, D. (1996) Cdc25 cell-cycle phosphatase as a target of c-myc. *Nature* 382:511–517
18. Kranenburg, O., van der Eb, A. and Zantema, A. (1996) Cyclin D1 is an essential mediator of apoptotic neuronal cell death. *EMBO J.* 15:46–54
19. Schrotor, M., Peitsch, M. C. and Tschopp, J. (1996) Increased p34cdc2-dependent kinase activity during apoptosis: A possible activation mechanism of DNAse I leading to DNA breakdown. *Eur. J. Cell Biol.* 69:143–150
20. Shi, L., Nishioka, W. K., Thng, J., Bradbury, E. M., Litchfield, D. W. and Greenberg, E. H. (1994) Premature p34cdc2 activation required for apoptosis. *Science* 263:1143–1145
21. Meikrantz, W., Gisselbrecht, S., Tam, S. W. and Schlegel, R. (1994) Activation of cyclin A-dependent protein kinases during apoptosis. *Proc. Natl. Acad. Sci. U.S.A.* 91:3754–3758
22. Ambrosini, G., Adida, C. and Altieri, D. C. (1997) A novel anti-apoptosis gene, Survivin, expressed in cancer and lymphoma. *Nature Med.* 3:917–921
23. Adida, C., Crotty, P. L., McGrath, J., Berrebi, D., Diebold, J. and Altieri, D. C. (1998) Developmentally regulated expression of the novel cancer anti-apoptosis gene Survivin in human and mouse differentiation. *Am. J. Pathol.* 152:43–49
24. Yarden, A. and Kinchi, A. (1986) Tumor necrosis factor reduces c-myc expression and cooperates with interferon-g in HeLa cells. *Science* 234:1419–1421
25. Adida et al. (1998) *Lancet*, Mar. 21, 1998.
26. Ambrosini et al., (1998) *J. Biol. Chem.* 273.
27. *Cancer Res.* (to be published).

What is claimed is:

1. A method of identifying an agent which modulates one or more interactions between Survivin and tubulin comprising the steps of:
   (a) contacting Survivin and tubulin in the presence of the agent; and
   (b) determining whether the agent modulates one or more interactions between Survivin and tubulin, thereby identifying an agent which modulates one or more interactions between Survivin and tubulin.

2. The method of claim 1, wherein step (b) comprises comparing one or more interactions between Survivin and tubulin in the presence of the agent to the same one or more interactions in the absence of the agent.

3. The method of claim 1, wherein a cell expressing Survivin and tubulin is contacted with the agent.

4. The method of claim 1, wherein the Survivin and tubulin are exposed to the agent in a cell-free environment.

5. The method of claim 1, wherein at least some of the tubulin is in polymerized form or in the form of microtubules.

6. The method of claim 1, wherein the agent is a Survivin peptide or small molecule mimetic thereof.

7. The method of claim 1, wherein the agent is a tubulin peptide or small molecule mimetic thereof.

8. The method of claim 1, wherein the one or more interactions comprise the binding of Survivin and tubulin.

9. A method of identifying an agent which modulates one or more interactions between Survivin and the mitotic spindles of a cell comprising the steps of:

(a) contacting a mitotically active cell with the agent;

(b) determining whether the agent modulates one or more interactions of Survivin with the mitotic spindles of the cell thereby identifying an agent which modulates one or more interactions of Survivin with the mitotic spindles.

10. The method of claim 9, wherein step (b) comprises comparing one or more interactions between Survivin and the mitotic spindles in the presence of the agent to the same one or more interactions in the absence of the agent.

11. The method of claim 10, wherein the one or more interactions comprise the binding of Survivin to the mitotic spindles.

12. The method of claim 11, wherein the binding of Survivin to the mitotic spindles is detected with an antibody which binds to Survivin.

13. The method of claim 1, wherein in step (a), Survivin is contacted with polymerized tubulin in the presence of the agent.

14. The method of claim 6, wherein the Survivin peptide or small molecule mimetic thereof binds tubulin.

15. The method of claim 7, wherein the tubulin peptide or small molecule mimetic thereof binds Survivin.

16. The method of claim 1, wherein in step (a), the agent is an antibody.

17. The method of claim 16, wherein the antibody binds Survivin.

18. The method of claim 16, wherein the antibody binds tubulin.

19. The method of claim 1, wherein step (b) comprises determining whether there is an increase or decrease in number of cells undergoing apoptosis relative to a control sample.

20. The method of claim 19, wherein the number of cells undergoing apoptosis increases or decreases by about 10%, 20%, 40%, 50% or more relative to a control sample.

21. The method of claim 1, wherein the tubulin is a tubulin isoform selected from the group consisting of α, β, or γ.

22. The method of claim 1, wherein the Survivin and tubulin are of isolated form.

23. The method of claim 1, wherein the Survivin and tubulin are of purified form.

24. The method of claim 1, wherein the Survivin or tubulin is of isolated form.

25. The method of claim 1, wherein the Survivin or tubulin is of purified form.

26. The method of claim 1, wherein step (a) is performed in the presence of caspase-3 and its substrate.

27. The method of claim 26, wherein the substrate is a DEVD-containing synthetic peptide.

28. The method of claim 1, wherein Survivin or tubulin is labeled.

29. The method of claim 1, wherein Survivin or tubulin is immobilized.

30. The method of claim 29, wherein Survivin or tubulin is immobilized using an antibody.

31. The method of claim 29, wherein Survivin or tubulin further comprises a protein or peptide fused in frame.

32. The method of claim 29, wherein Survivin or tubulin is covalently attached to a conjugate.

33. The method of claim 32, wherein the conjugate is biotin.

34. The method of claim 1, wherein step (b) comprises detecting apoptosis.

35. The method of claim 34, wherein the Survivin is a Survivin mutant selected from the group consisting of Leu64→Ala, Pro26→Ala, and Cys84→Ala.

36. The method of claim 34, wherein the Survivin further comprises a carboxyl-terminal Ring of a X-Linked Inhibitor of Apotosis Protein (XIAP).

37. The method of claim 34, wherein the agent is a Survivin peptide, or small molecule mimetic thereof.

38. The method of claim 37, wherein the Survivin peptide or small molecule mimetic thereof binds tubulin.

39. The method of claim 34, wherein the agent is a tubulin peptide, or small molecule mimetic thereof.

40. The method of claim 39, wherein the tubulin peptide or small molecule mimetic thereof binds Survivin.

\* \* \* \* \*

UNITED STATES PATENT AND TRADEMARK OFFICE
CERTIFICATE OF CORRECTION

| | | |
|---|---|---|
| PATENT NO. | : 6,346,389 B1 | Page 1 of 1 |
| APPLICATION NO. | : 09/283144 | |
| DATED | : February 12, 2002 | |
| INVENTOR(S) | : Dario C. Altieri | |

It is certified that error appears in the above-identified patent and that said Letters Patent is hereby corrected as shown below:

In Column 1, line 14, before the section entitled "FIELD OF THE INVENTION", please insert the following section:

--GOVERNMENT SUPPORT
This invention was made with government support under HL054131 and HL043773 awarded by National Institute of Health. The government has certain rights in the invention.--

Signed and Sealed this

Fourth Day of December, 2012

David J. Kappos
*Director of the United States Patent and Trademark Office*

SEQUENCE LISTING

```
<160> NUMBER OF SEQ ID NOS: 15

<210> SEQ ID NO 1
<211> LENGTH: 417
<212> TYPE: DNA
<213> ORGANISM: Homo sapiens
<220> FEATURE:
<223> OTHER INFORMATION: DNA sequence of proximal 5' flanking region of
      Survivin gene
<220> FEATURE:
<221> NAME/KEY: CDS
<222> LOCATION: (291)..(401)

<400> SEQUENCE: 1
gagccactgc acccggcctg cacgcgttct ttgaaagcag tcgaggggc gctaggtgtg      60 ggcagggacg agctggcgcg gcgtcgctgg gtgcaccgcg accacgggca gagccacgcg    120
gcgggaggac tacaactccc ggcacaccc gcgccgcccc gcctctactc ccagaaggcc    180 gcgggggtg gaccgcctaa gagggcgtgc gctcccgaca tgccccgcgg cgcgccatta    240
accgccagat ttgaatcgcg ggagccgttg gcagaggtgg cggcggcggc atg ggt      296
                                                        Met Gly
                                                          1 gcc ccg acg ttg ccc cct gcc tgg cag ccc ttt ctc aag gac cac cgc    344
Ala Pro Thr Leu Pro Pro Ala Trp Gln Pro Phe Leu Lys Asp His Arg
         5                  10                  15 atc tct aca ttc aag aac tgg ccc ttc ttg gag ggc tgc gcc tgc acc    392
Ile Ser Thr Phe Lys Asn Trp Pro Phe Leu Glu Gly Cys Ala Cys Thr
     20                  25                  30 ccg gag cgg gtgagactgc ccggcc                                      417
Pro Glu Arg
 35

<210> SEQ ID NO 2
<211> LENGTH: 426
<212> TYPE: DNA
<213> ORGANISM: Homo sapiens
<220> FEATURE:
<223> OTHER INFORMATION: Nucleotide sequence of open reading frame
      encoding Survivin
```

<400> SEQUENCE: 2

```
atgggtgccc cgacgttgcc ccctgcctgg cagcccttc tcaaggacca ccgcatctct      60
acattcaaga actggccctt cttggagggc tgcgcctgca ccccggagcg gatggccgag     120
gctggcttca tccactgccc cactgagaac gagccagact tggcccagtg tttcttctgc     180
ttcaaggagc tggaaggctg ggagccagat gacgacccca tagaggaaca taaaaagcat     240
tcgtccggtt gcgctttcct ttctgtcaag aagcagtttg aagaattaac ccttggtgaa     300
ttttgaaac tggacagaga aagagccaag aacaaaattg caaaggaaac caacaataag     360
aagaaagaat ttgaggaaac tgcgaagaaa gtgcgccgtg ccatcgagca gctggctgcc     420
atggat                                                                426
```

<210> SEQ ID NO 3
<211> LENGTH: 142
<212> TYPE: PRT
<213> ORGANISM: Homo sapiens
<220> FEATURE:
<223> OTHER INFORMATION: Amino acid sequence of Survivin

<400> SEQUENCE: 3

```
Met Gly Ala Pro Thr Leu Pro Pro Ala Trp Gln Pro Phe Leu Lys Asp
  1               5                  10                  15
His Arg Ile Ser Thr Phe Lys Asn Trp Pro Phe Leu Glu Gly Cys Ala
                 20                  25                  30
Cys Thr Pro Glu Arg Met Ala Glu Ala Gly Phe Ile His Cys Pro Thr
             35                  40                  45
Glu Asn Glu Pro Asp Leu Ala Gln Cys Phe Phe Cys Phe Lys Glu Leu
         50                  55                  60
Glu Gly Trp Glu Pro Asp Asp Asp Pro Ile Glu Glu His Lys Lys His
  65                 70                  75                  80
Ser Ser Gly Cys Ala Phe Leu Ser Val Lys Lys Gln Phe Glu Glu Leu
                 85                  90                  95
Thr Leu Gly Glu Phe Leu Lys Leu Asp Arg Glu Arg Ala Lys Asn Lys
                100                 105                 110
Ile Ala Lys Glu Thr Asn Asn Lys Lys Lys Glu Phe Glu Glu Thr Ala
            115                 120                 125
Lys Lys Val Arg Arg Ala Ile Glu Gln Leu Ala Ala Met Asp
        130                 135                 140
```

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Primer
      for cloning Survivin construct

<400> SEQUENCE: 4

```
cgcggatccg cgttctttga aagcagtc                                         28
```

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Primer
      for cloning Survivin construct

<400> SEQUENCE: 5
cccaagcttt gccgccgccg ccacctct                                    28

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Primer
      for cloning Survivin construct

<400> SEQUENCE: 6
cccaagcttc aaatctggcg gttaatgg                                    28

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Primer
      for cloning Survivin construct

<400> SEQUENCE: 7
atcgcaagct tggcggcatg ggtgcc                                      26

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Primer
      for cloning Survivin construct

<400> SEQUENCE: 8
ctgaattcaa ccaagggtta attcttc                                     27

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer
      for cloning Survivin construct

<400> SEQUENCE: 9
aagaactggg ccttcttgga g                                           21

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Primer
      for cloning Survivin construct

<400> SEQUENCE: 10
tgcttcaagg aggcggaagg ctggga                                      26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Primer
      for cloning Survivin construct

<400> SEQUENCE: 11

```
cattcgtccg gtgccgcttt cctttc                                              26
```

```
<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:  Primer
      for cloning Survivin construct

<400> SEQUENCE: 12
acggatccag agaagatgac tttttaac                                            28

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence:  Primer
      for cloning Survivin construct

<400> SEQUENCE: 13
acgaattcaa catgcctact atagag                                              26

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:  Probe to
      detect Survivin in northern blots

<400> SEQUENCE: 14
atgacctcca gaggtttc                                                       18

<210> SEQ ID NO 15
<211> LENGTH: 37
<212> TYPE: PRT
<213> ORGANISM: Homo sapiens
<220> FEATURE:
<223> OTHER INFORMATION: Amino acid sequence from beginning of coding
      region of Survivin gene

<400> SEQUENCE: 15

Met Gly Ala Pro Thr Leu Pro Pro Ala Trp Gln Pro Phe Leu Lys Asp
 1               5                  10                  15

His Arg Ile Ser Thr Phe Lys Asn Trp Pro Phe Leu Glu Gly Cys Ala
            20                  25                  30

Cys Thr Pro Glu Arg
         35
```